United States Patent [19]
Bennett et al.

[11] Patent Number: 6,001,651
[45] Date of Patent: Dec. 14, 1999

[54] ANTISENSE MODULATION OF LFA-3

[75] Inventors: C. Frank Bennett; Thomas P. Condon, both of Carlsbad; Shin Cheng Flournoy, San Diego, all of Calif.; Jordan S. Pober, Guilford; Weillie Ma, Hamden, both of Conn.

[73] Assignee: Isis Pharmaceuticals Inc., Carlsbad, Calif.

[21] Appl. No.: 09/045,106

[22] Filed: Mar. 20, 1998

[51] Int. Cl.$^6$ .......................... C12N 15/85; C12N 21/04; C12N 15/11; C12Q 1/68

[52] U.S. Cl. .......................... 435/375; 435/6; 435/91.1; 435/371; 536/23.1; 536/24.31; 536/24.33; 536/24.5

[58] Field of Search .................. 435/6, 91.1, 320.1, 435/371, 375, 440; 536/23.1, 23.5, 24.31, 24.5; 514/44

[56] References Cited

U.S. PATENT DOCUMENTS

| | | | |
|---|---|---|---|
| 4,956,281 | 9/1990 | Wallner et al. | 435/69.3 |
| 5,185,441 | 2/1993 | Wallner et al. | 435/356 |
| 5,354,665 | 10/1994 | Wallner et al. | 435/69.3 |
| 5,547,853 | 8/1996 | Wallner et al. | 435/69.1 |
| 5,556,943 | 9/1996 | Yamashita et al. | 530/350 |

FOREIGN PATENT DOCUMENTS

| | | |
|---|---|---|
| WO 91/13981 | 9/1991 | WIPO . |
| WO 92/04463 | 3/1992 | WIPO . |
| 0 786 255 A1 | 6/1992 | WIPO . |
| WO 92/16563 | 10/1992 | WIPO . |
| WO 93/06852 | 4/1993 | WIPO . |
| WO 93/06866 | 4/1993 | WIPO . |
| WO95/06165 | 2/1996 | WIPO . |
| WO 96/33217 | 10/1996 | WIPO . |

OTHER PUBLICATIONS

Milligan Et Al. J. Medicinal Chemistry. vol. 36, 1923–1937 (Jul. 09, 1993).

Mitsuhashi. J. Gastroenterol. vol. 32, 282–287 (1997).

Gewirtz Et Al. PNAS. vol. 93, 3161–3163 (Apr. 1996).

Rojanasakul. Adv. Drug Delivery Reviews. vol. 18, 115–131 (Jan. 1996).

Branch. TIBS. vol. 23, 45–50 (Feb. 1998).

Albelda, et al., "Adhesion molecules and inflammatory injury", FASEB J., 1994, 8, 504.

Seed, "An LFA–3 cDNA encodes a phospholipid–linked membrane protein homologous to its receptor CD2", Nature, 1987, 329, 840.

Sanchez–Madrid, et al., "Three distinct antigens associated with human T–lymphocyte–mediated cytolysis: LFA–1. LFA–2, and LFA–3", Proc. Natl. Acad. Sci. U.S.A., 1982, 79, 7489.

Sultan, et al., "Blockade of CD–LFA–3 interactions protects human skin allografts in immunodeficient mouse/human chimeras", Nature Biotech., 1997, 15, 759.

Makgoba, et al., "The CD2–LFA–3 and LFA–1 1–ICAM pathways: relevance to T–cell recognition", Immunology Today, 1989, 10, 417.

Bierer, et al., "T cell adhesion molecules", FASEB J., 1988, 2, 2584.

Dustin, et al., "Role of Lymphocyte Adhesion Receptors in Transient Interactions And Cell Locomotion", Annu. Rev. Immunol., 1991, 9, 27.

Wallner, et al. "Primary Structure of Lymphocyte Function–Associated Antigen 3 (LFA–3) The Ligand of the T Lymphocyte CD2 Glycoprotein", J. Exp. Med., 1987, 166, 923.

*Primary Examiner*—John L. LeGuyader
*Assistant Examiner*—Mark L. Shibuya
*Attorney, Agent, or Firm*—Law Offices of Jane Massey Licata

[57] ABSTRACT

Compositions and methods for the treatment and diagnosis of diseases or disorders amenable to treatment through modulation of expression of a nucleic acid encoding a lymphocyte function associated antigen 3 (LFA-3; also known as CD58) protein are provided.

5 Claims, 5 Drawing Sheets

```
CGACGAGCCATGGTTGCTGGGAGCGACGCGGGGGCGGGCCCTGGGGTCCTCAGCGTGCTGCCTGCTGCACTGCTTTGG    80
          CCAACGACCCTCGCTGCGCC         CCAGGAGTCGCACCAGACGG               (16371 & 16910)
                                                                              (16372)

TTTCATCAGCTGTGTTTTCCCAACAAATATATGGTGTGTTGTGTATGGAATGTAACTTTCCATGTACCAAGCAATGTGCCTT  160
                                          ACATGGTTCGTTACACGGAA              (16373)

TAAAAGAGGTCCTATGGAAAAAACAAAGGATAAAGTTGCAGAACTGGAAAATTCTGAATTCAGAGCTTTCTCATCTTTT    240

AAAAATAGGGTTTATTTAGACACTGTGTCAGGTAGCCTCACTATCTACAACTTAACATCATCAGATGAAGATGAGTATGA   320
                              GTGACACAGTCCATCGGAGT                          (16374, 16909 &
                                                                              17159)

AATGGAATCGCCAAATATTACTGATATACCATGAAGTTCTTTCTTTATGTGCTTGAGTCTCTTCCATCTCCCACACTAACTT 400

GTGCATTGACTAATGGAAGCATTGAAGTCCAATGCATGATACCAGAGCATTACAACAGCCATCGAGGACTTATAATGTAC   480

TCATGGGATTGTCCTATGGAGCAATGTAAACGTAACTCAACCAGTATATATTTTAAGATGGAAAATGATCTTCCACAAAA   560
```

AATACAGTGTACTCTTAGCAATCCATTATTTAATACAACATCATCAATCATTTTGACAACCTGTATCCAAGCAGCGGTC

720

ATTCAAGACACAGATATGCACTTATACCCATACCATTAGCAGTAATTACACACATGTATTGTGCTGTATATGAATGGTATT 800
                                                                                         (16375)
                                                                                         (16376)
                                                                                         (16377)

CTGAAATGTGACAGAAAACCAGACAGAACCAACTCCAATTGATTGGTAACAGAAGATGAAGACAACAGCATAACTAAATT
                                 GTCTGTCTCTTGGTTGAGGTTA
                                       ACTAACCATTGTCTTCTACT
                                                                        CTGTTGTCGTATTGATTTAA 880
                                                                                         (16378)

ATTTTAAAAACTAAAAAGCCATCTGATTTCTCATTTGAGTATTACAATTTTTGAACAACTGTTGGAAATGTAACTTGAAG
                                                                CTTGTTGACAACCTTTACAT 960
                                                                                         (16379)
                                                                                         (16380)
                                                                                         (16381)

CAGCTGCTTTAAGAAGAAATACCCACTAACAAAGAACAAGCATTAGTTTTGGCTGTCATCAACTTATTATATGACTAGGT
                                    GGTGATTGTTTCTTGTTCGT
                                                         CCGACAGTAGTTGAATAATA
                                                                              TATACTGATCCA 1040
                                                                                         (16381)

GCTTGCTTTTTTGTCAGTAAATTGTTTTTACTGATGATGTAGATACTTTTGTAAATAAATGTAAATATGTACACAAGTG
CGAACGAA
```

FIGURE 1B

ANTISENSE MODULATION OF LFA-3

FIELD OF THE INVENTION

The present invention provides compositions and methods for detecting and modulating levels of lymphocyte function-associated antigen 3 (LFA-3) proteins, including human LFA-3 (also known as CD58 antigen). In particular, the invention relates to antisense compounds specifically hybridizable with nucleic acids encoding LFA-3 proteins.

LFA-3 mediates particular cell—cell interactions. Accordingly, modulation of the expression of LFA-3 allows for the control of such cell—cell interactions and resulting effects such as, for example, inflammation. The invention is thus directed to diagnostic methods for detecting, and prophylactic and therapeutic methods for preventing or inhibiting, respectively, LFA-3-mediated processes. Furthermore, this invention is directed to treatment of conditions associated with abnormal expression of LFA-3 proteins. This invention also relates to therapies, diagnostics, and research reagents for disease states or disorders which respond to modulation of the expression of LFA-3 proteins. Inhibition of the hyperproliferation of cells, and corresponding prophylactic, palliative and therapeutic effects result from treatment with the antisense compounds of the invention.

BACKGROUND OF THE INVENTION

Cell—cell interactions are a feature of a variety of biological processes. In the activation of the immune response, for example, one of the earliest detectable events in a normal inflammatory response is adhesion of leukocytes to the vascular endothelium, followed by migration of leukocytes out of the vasculature to the site of infection or injury. The adhesion of leukocytes to vascular endothelium is an obligate step in their migration out of the vasculature (for a review, see Albelda et al., *FASEE J.*, 1994, 8, 504). As is well known in the art, cell—cell interactions are also critical for propagation of both B-lymphocytes and T-lymphocytes resulting in enhanced humoral and cellular immune responses, respectively.

In several instances, the adhesion of one cell type to another is mediated by interactions between specific proteins, termed "adhesion molecules," located on the surface membrane of cells. The interaction between adhesion molecules is similar to classical receptor ligand interactions with the exception that the ligand is fixed to the surface of a cell instead of being soluble. One group of related (by peptide sequence), biologically significant molecules mediating cell—cell interactions are known in the art as CAMs (cellular adhesion molecules). CAMs include, for example, several intercellular adhesion molecules (i.e., ICAM-1, ICAM-2 and ICAM-3), endothelial leukocyte adhesion molecule 1 (ELAM-1), vascular cell adhesion molecule 1 (VCAM-1), and platelet endothelial cell adhesion molecule 1 (PECAM-1). The CAM family is in turn a part of the immunoglobulin superfamily of genes (Newman et al., *Science*, 1990, 247, 1219).

In cell:cell interactions, a given cellular adhesion molecule present on a first cell binds one or more ligands present on a second cell. For example, ICAM-1 binds LFA-1, LFA-3 binds CD2, etc. Such interactions may be simply represented as follows:

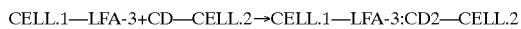

The binding of a given cellular adhesion molecule to its ligand can have many results, including (1) facilitating the ability of the two cells to remain in close contact for a period of time, during which molecules (e.g., antigens) can be passed directly from one cell to the other and/or (2) initiating a cellular response in, for example, the second cell via a conformational or chemical change in the ligand of the second cell that results from the ligand's interaction with the first cell's adhesion molecule (i.e., signal transduction). In the latter instance, a free (i.e., not associated with a cell) soluble form of the appropriate adhesion molecule may be capable of binding to the surface ligands of the second cell and thereby evoking the same or similar cellular response. Such soluble isoforms of adhesion molecules may also be produced in vivo in order to competitively bind with the membrane-bound ligand and thus reduce or inhibit cell:cell interactions, and/or to effect cell:cell de-adhesion. Using LFA-3 and CD2 as examples, such reactions may be simply diagramed as follows, wherein "sCD2" indicates a soluble form of CD2 present in excess:

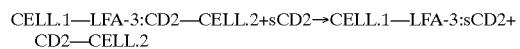

As is known in the art, cell:cell interactions play an important role in the activation of thymus-derived lymphocytes (T cells), which are regulatory and/or effector cells in a variety of immune responses. That is, some T cells (e.g., helper cells) act to regulate other cells of the immune system by, e.g., producing and releasing factors that stimulate such other cells to effect molecular immunoreactive activities. Other T cells [e.g., cytotoxic, cytolytic or natural killer (NK) cells] directly effect immunoreactive activities by, e.g., lysing target cells bearing a foreign or abnormal antigen. In either event, the stimulation and antigen specificity of T cells in an immune response is mediated by cell:cell interactions between a T cell and, e.g., an antigen presenting cell (APC) (Bierer et al., *FASEB J.*, 1988, 2, 2584). At a molecular level, these cell:cell interactions are mediated by adhesion molecules present on T cells and APCs (Bierer et al., *FASEB J.*, 1988, 2, 2584; Makgoba et al., *Immunol. Today*, 1989, 10, 417).

Several types of adhesion molecules are implicated in mediating interactions between T cells and APCs. These include at least three lymphocyte function associated antigens (LFA-1, LFA-2 and LFA-3; Sanchez-Madrid et al., *Proc. Natl. Acad. Sci. U.S.A.*, 1982, 79, 7489) and ICAMs (including ICAM-1, ICAM-2 and ICAM-3). The present invention is drawn to modulators of LFA-3 function, the ligand/receptor of which is CD2. CD2 is expressed primarily on T cells, including helper and NK cells, while LFA-3 is expressed on all human cells except thymocytes and some T cells (Bierer et al., *FASEB J.*, 1988, 2, 2584).

LFA-3 proteins are glycoproteins expressed on the surfaces of a variety of cell types (for reviews of LFA-3 and related proteins, see Dustin et al., *Annu. Rev. Immunol.*, 1991, 9, 27). LFA-3 plays a role in mediating thymocyte interactions with thymic epithelial cells, and antigen-dependent and—independent interactions of T lymphocytes with target cells and APCs (Wallner et al., *J. Exp. Med.*, 1987, 166, 923). This interaction can also enhance major histocompatibility complex (MHC) T cell recognition (Selvaraj et al., *Nature*, 1987, 326, 400). LFA-3 is also associated with some hyperproliferative diseases, such as myeloma (Cook et al., *Acta Haematol.*, 1997, 97, 81; Tatsumi et al., *Jpn. J. Cancer Res.*, 1996, 87, 837).

Furthermore, LFA-3 is upregulated in cells infected with, or enhances the replication of, certain viruses, for example, cytomegalovirus (Grundy et al., *Immunol.*, 1993, 78, 405).

Due to LFA-3's involvement in cellular processes associated with immune responses, tumorigenesis and other disease states, it is hoped that inhibitors of LFA-3 expression would provide a novel therapeutic class of immunosuppressive and/or anti-inflammatory and/or anticancer agents with activity towards (1) autoimmune disorders such as multiple sclerosis, particularly autoimmune disorders of the thyroid such as Graves' disease, and undesired immune responses, such as, for example, those that occur in graft versus host disease (GVHD); (2) a variety of inflammatory diseases or disorders with an inflammatory or T cell-mediated component such as various forms of arthritis; allograft rejections; asthma; inflammatory diseases of the bowel, including Crohn's disease; various dermatological conditions such as psoriasis; and the like, and (3) a variety of hyperproliferative diseases or disorders including, but not limited to, cancers, tumors, and the growth and spreading (metastasis) thereof.

To date, there are no known therapeutic agents which effectively prevent the expression of LFA-3. Current agents which affect cellular adhesion molecules include monoclonal antibodies and polypeptide soluble forms of the ligands of adhesion molecules. Monoclonal antibodies to LFA-3 may prove to be useful for the treatment of acute inflammatory response due to expression of LFA-3. However, the binding of antibodies to membrane-bound LFA-3 may mimic ligand (CD2) binding and thus stimulate signal transduction, even though CD2 binding is blocked; compounds that reduce or inhibit the expression of LFA-3, such as the antisense compounds of the invention, should block both ligand and signal transduction. Moreover, with chronic treatment, the host animal develops antibodies against the monoclonal antibodies thereby limiting their usefulness. In addition, monoclonal antibodies are large proteins which may have difficulty in gaining access to the inflammatory site. Polypeptide forms of the cell adhesion molecules suffer from many of the same limitations as monoclonal antibodies in addition to the expense of their production and their low binding affinity. Moreover, LFA-3 is transmembrane or membrane-bound protein, and polypeptides derived from LFA-3 are often insoluble in aqueous solution, limiting their therapeutic potential (Dustin et al., *Annu. Rev. Immuno.*, 1991, 9, 27). Thus, there is a long felt need for molecules which effectively inhibit LFA-3. Antisense oligonucleotides avoid many of the pitfalls of current agents used to block the effects of LFA-3. It has been found that such antisense compounds can modulate the expression of LFA-3 proteins.

RELATED ART

Published PCT patent applications WO 92/04463 and WO 92/16563 disclose monoclonal antibodies against LFA-3 and indicate that such antibodies may be of use in treating and diagnosing rheumatoid arthritis, autoimmune diseases and other diseases.

Published PCT patent applications Wo 91/13981, Wo 93/06852 and WO 96/33217 disclose LFA-3 protein and fragments thereof and indicate that these polypeptides may be used to inhibit autoimmune diseases and transplant rejection.

Published PCT patent application WO 93/06866 discloses methods of preventing or treating skin conditions using non-antisense based inhibitors of the LFA-3:CD2 interaction.

Published EPO patent application EP 0 786 255 Al discloses soluble forms and conjugates of LFA-3 that bind CD2, or of CD2 that bind LFA-3, and indicates that these compounds can be used to improve allograft or xenograft tolerance.

U.S. Pat. Nos. 4,956,281, 5,185,441 and 5,354,665 disclose nucleotide sequences encoding LFA-3 and methods of producing LFA-3 polypeptides.

U.S. Pat. No. 5,547,853 discloses peptides corresponding to the CD2 binding domain of LFA-3 indicated to be useful for diagnostic and therapeutic purposes.

U.S. Pat. No. 5,556,943 discloses sheep LFA-3 protein sequences and derivatives thereof, and indicates that such polypeptides are useful for treating leukemias.

SUMMARY OF THE INVENTION

In accordance with the present invention, antisense compounds are provided which specifically hybridize with a nucleic acid encoding a LFA-3 protein. Certain antisense compounds of the invention are designed to bind either directly to mRNA transcribed from, or to a selected DNA portion of, a gene that encodes a LFA-3 protein, thereby modulating the expression thereof. In particular embodiments of the invention, the LFA-3 protein, and the gene encoding it, are those of a mammal including a human. Pharmaceutical compositions comprising the antisense compounds of the invention, and various methods of using the antisense compounds of the invention, are also herein provided.

BRIEF DESCRIPTION OF THE DRAWINGS

FIGS. 1A and 1B show the sequence of a cDNA encoding human LFA-3 (SEQ ID NO: 1; GenBank Accession no. Y00636, locus name "HSLFA3") and the locations and sequences of antisense oligonucleotides described in the Examples. The cDNA sequence is written from 5' to 3' and has vertical marks indicating every tenth base; the cumulative number of bases in the sequence is given in bold to the right of each line. The start (ATG) and stop (TGA) codons are emboldened and double-underlined. The nucleotide base sequences of the antisense oligonucleotides are written from 3' to 5' to demonstrate their complementary nature, and their ISIS number is given in parentheses to the right of each line.

DETAILED DESCRIPTION OF THE INVENTION

Figure 2A:
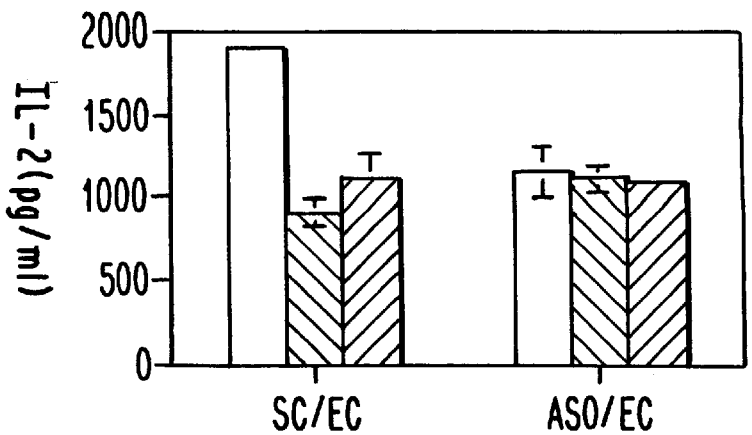
FIG. 2 shows that pretreatment of human endothelial cells with antisense oligonucleotides inhibits costimulation of cytokine production from PHA-activated $CD4^+$ T cells. Symbols and abbreviations: "SC," scrambled control oligonucleotide (ISIS 17092); "ASO," active antisense oligonucleotide (ISIS 16374); open boxes, no monoclonal antibody added; hatched boxes, monoclonal antibody to LFA-3 added; filled boxes, monoclonal antibody to CD2 added.

Oligonucleotides may comprise nucleotide sequences sufficient in identity and number to effect specific hybridization with a particular nucleic acid. Such oligonucleotides are commonly described as "antisense." Antisense oligonucleotides are commonly used as research reagents, diagnostic aids, and therapeutic agents. It has been discovered that genes encoding lymphocyte function associated antigen-3 (LFA-3; also known as CD58 antigen) proteins, including human LFA-3, are particularly amenable to this approach. More specifically, the present invention is directed to antisense compounds, including oligonucleotides, that modulate the expression of LFA-3.

Methods of modulating the expression of LFA-3 proteins with antisense compounds are provided herein and are believed to be useful both therapeutically and diagnostically as a consequence of the association between LFA-3 expression and certain hyperproliferative and inflammatory disorders. These methods are also useful as tools, for example, in the detection and determination of the role of LFA-3 in various cell functions and physiological processes and conditions, and for the diagnosis of conditions associated with such expression and activation.

As a consequence of the association between LFA-3 and normal and abnormal cell—cell interactions, inhibition of the expression of LFA-3 proteins is expected to lead to, for example, the inhibition of a variety of undesired immunoresponsive events and tumorigenic and/or metastatic events and, accordingly, results in modulation of the undesirable consequences of such events. Such modulation is desirable for treating (i.e., providing prophylactic, palliative and/or therapeutic effects) various inflammatory and hyperproliferative disorders or diseases. Such inhibition of LFA-3, and other CAMs, is further desirable for preventing or modulating the development of such diseases or disorders in an animal suspected of being, or known to be, prone to such diseases or disorders.

The present invention also comprises methods of inhibiting a variety of LFA-3-mediated inflammatory and tumorigenic and/or metastatic events using the antisense compounds of the invention. Methods of treating conditions in which abnormal or excessive LFA-3 expression and/or LFA-3-mediated inflammation occurs are also provided. These methods employ the antisense compounds of the invention and are believed to be useful both therapeutically and as clinical research and diagnostic tools. The oligonucleotides of the present invention may also be used for research purposes. Thus, the specific hybridization exhibited by the oligonucleotides of the present invention may be used for assays, purifications, cellular product preparations and in other methodologies which may be appreciated by persons of ordinary skill in the art.

The present invention employs antisense compounds which modulate the function of DNA or messenger RNA (mRNA) encoding a protein (LFA-3) the modulation of which is desired and ultimately regulate the expression of the protein. Hybridization of an antisense oligonucleotide with its mRNA target interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expression.

It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene associated with hyperproliferative disorders. The targeting process also includes determination of a site or sites within this gene for the oligonucleotide interaction to occur such that the desired effect, either detection or modulation of expression of the protein, will result. Once the target site or sites have been identified, oligonucleotides are chosen which are sufficiently complementary to the target, i.e., hybridize sufficiently well and with sufficient specificity to give the desired effect.

Generally, there are several regions of a gene that may be targeted for antisense modulation: the 5' "cap," which comprises an N7-methylated guanosine residue joined to the most 5' residue of the mRNA via a triphosphate linkage (Baker, Chapter 3 In: *Antisense Research and Applications*, Crooke et al., eds., CRC Press, Boca Raton, Fla, 1993, pages 37–53); the 5' untranslated region (hereinafter, the "5'-UTR"), the translation initiation codon region (hereinafter, the "AUG" region), the open reading frame (hereinafter, the "ORF") or "coding region," the translation termination codon region (hereinafter, the "stop codon" region or simply "stop" for short) and the 3' untranslated region (hereinafter, the "3'-UTR"). As is known in the art, these regions are arranged in a typical messenger RNA molecule in the following order (left to right, 5' to 3'): cap, 5'-UTR, AUG, ORF, stop codon, 3'-UTR. As is known in the art, although some eukaryotic transcripts are directly translated, many ORFs contain one or more sequences, known as "introns," which are excised from a transcript before it is translated; the expressed (unexcised) portions of the ORF are referred to as "exons" (Alberts et al., *Molecular Biology of the Cell*, 1983, Garland Publishing Inc., New York, pp. 411–415). Furthermore, because many eukaryotic ORFs are a thousand nucleotides or more in length, it is often convenient to subdivide the ORF into, e.g., the 5' ORF region, the central ORF region, and the 3' ORF region. In some instances, an ORF contains one or more sites that may be targeted due to some functional significance in vivo. Examples of the latter types of sites include intragenic stem-loop structures (see, e.g., U.S. Pat. No. 5,512,438) and, in unprocessed mRNA molecules, intron/exon splice sites.

Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., *Growth Factors*, 1990, 4, 45; Gelbert et al., *Somat. Cell. Mol. Genet.*, 1990, 16, 173; Gold and Stormo, in: *Escherichia coli and Salmonella typhimurium: Cellular and Molecular Biology*, Vol. 2, 1987, Neidhardt et al., eds., American Society for Microbiology, Washington, D.C., p. 1303). Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences. In the context of the invention, "start codon" and "translation initiation codon" refer to the codon or codons that are used in vivo to initiate translation of an mRNA molecule transcribed from a gene encoding a LFA-3 protein, regardless of the nucleotide sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation region" refer to a portion of such an mRNA or gene that encompasses about 50 contiguous (adjacent) nucleotides in either direction (i.e., 5' or 3') from a translation initiation codon. Similarly, the terms "stop codon region" and "translation termination region" refer to a portion of such an mRNA or gene that encompasses about 50 contiguous (adjacent) nucleotides in either direction (i.e., 5' or 3') from a translation termination codon.

The remainder of the Detailed Description relates in more detail the (1) Antisense Compounds of the Invention and (2) Bioequivalents and (3) Exemplary Utilities thereof, as well as (4) Pharmaceutical Compositions comprising the Antisense Compounds of the Invention and (5) Methods of Administration thereof.

1. Antisense Compounds of the Invention

The present invention employs antisense compounds that modulate LFA-3 proteins. The term "antisense compounds" (a) specifically includes synthetic oligonucleotides, as well as peptide nucleic acids (PNAs), having a nucleobase sequence specifically hybridizable with a nucleic acid encoding a LFA-3 protein and (b) specifically excludes ribozymes and nucleic acids of biological origin. In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. The antisense compounds of the invention are synthesized in vitro and do not include antisense compositions of biological origin, or genetic vector constructs designed to direct the in vivo synthesis of antisense molecules.

The antisense compounds in accordance with this invention preferably comprise from about 8 to about 30 nucleobases, more preferably from about 12 to about 28 and most preferably from about 20 to about 26 nucleobases. Particularly preferred antisense compounds are antisense oligonucleotides. A discussion of antisense oligonucleotides and some desirable modifications can be found in De Mesmaeker et al., Acc. Chem. Res., 1995, 28, 366.

An oligonucleotide is a polymer of a repeating unit generically known as a nucleotide. An unmodified (naturally occurring) nucleotide has three components: (1) a nitrogen-containing heterocyclic base linked by one of its nitrogen atoms to (2) a 5-pentofuranosyl sugar and (3) a phosphate esterified to one of the 5' or 3' carbon atoms of the sugar. When incorporated into an oligonucleotide chain, the phosphate of a first nucleotide is also esterified to an adjacent sugar of a second, adjacent nucleotide via a 3'-5' phosphate linkage.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be further joined to form a circular structure, however, within the context of the invention, open linear structures are generally preferred.

Within the oligonucleotide structure, the phosphate groups are commonly referred to as forming the intersugar "backbone" of the oligonucleotide. The normal linkage or backbone of RNA and DNA is a 3' to 5' phosphodiester linkage. The backbone of an oligonucleotide (or other antisense compound) positions a series of bases in a specific order; the written representation of this ordered series of bases, usually written in 5' to 3' order unless otherwise indicated, is known as a nucleotide or nucleobase sequence.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other.

"Specifically hybridizable" and "complementary" are thus terms which are used to indicate a sufficient degree of complementarity or precise pairing such that stable and specific binding occurs between the oligonucleotide and the DNA or RNA target. An oligonucleotide is specifically hybridizable to its target sequence due to the formation of base pairs between specific partner nucleobases in the interior of a nucleic acid duplex. Among the naturally occurring nucleobases, guanine (G) binds to cytosine (C), and adenine (A) binds to thymine (T) or uracil (U). In addition to the equivalency of U (RNA) and T (DNA) as partners for A, other naturally occurring nucleobase equivalents are known, including 5-methylcytosine and 5-hydroxymethylcytosine (HMC) (C equivalents), and 5-hydroxymethyluracil (U equivalent). Furthermore, synthetic nucleobases which retain partner specificity are known in the art and include, for example, 7-deaza-Guanine, which retains partner specificity for C. Thus, an oligonucleotide's capacity to specifically hybridize with its target sequence will not be altered by a chemical modification to a nucleobase in the nucleotide sequence of the oligonucleotide which does not impact its specificity for a partner nucleobase in the target nucleic acid.

It is understood in the art that the nucleobase sequence of an oligonucleotide or other antisense compound need not be 100% complementary to its target nucleic acid sequence to be specifically hybridizable. An antisense compound is specifically hybridizable to its target nucleic acid when there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under assay conditions.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. The specificity and sensitivity of oligonucleotides is also harnessed by those of skill in the art for therapeutic uses. Specific examples of preferred anlisense compounds useful in this invention include oligonucleotides containing modified backbones or non-natural intersugar linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their intersugar backbone can also be considered to be oligonucleosides.

Specific oligonucleotide chemical modifications are described in the following subsections. It is not necessary for all positions in a given compound to be uniformly modified, and in fact more than one of the following modifications may be incorporated in a single antisense compound or even in a single residue thereof, for example, at a single nucleoside within an oligonucleotide.

A. Modified Linkages

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalklyphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States Patents that teach the preparation of the above phosphorus atom containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Preferred modified oligonucleotide backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the intersugar linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., =Science, 1991, 254, 1497.

Most preferred embodiments of the invention are oligonucleotides with phosphorothioate backbones and oligonucleosides with heteroatom backbones, and in particular $-CH_2-NH-O-CH_2-$, $-CH_2-N(CH_3)-O-CH_2-$ [known as a methylene (methylimino) or MMI backbone], $-CH_2-O-N(CH_3)-CH_2-$, $-CH_2-N(CH_3)-N(CH_3)-CH_2-$ and $-O-N(CH_3)-CH_2-CH_2-$ [wherein the native phosphodiester backbone is represented as $-O-P-O-CH_2-$] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

B. Modified Nucleobases

The compounds of the invention may additionally or alternatively comprise nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the *Concise Encyclopedia Of Polymer Science And Engineering*, pages 858–859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289–302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Id., pages 276–278) and are presently preferred base substitutions, even more particularly when combined with 2'-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; and 5,681,941, each of which is herein incorporated by reference, and U.S. patent application Ser. No. 08/762,488, filed on Dec. 10, 1996, also herein incorporated by reference.

C. Sugar Modifications

The antisense compounds of the invention may additionally or alternatively comprise one or more substituted sugar moieties. Preferred oligonucleotides comprise one of the following at the 2' position: OH; F; O—, S—, or N-alkyl, O—, S—, or N-alkenyl, or O, S— or N-alkynyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, $OCN$, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy [2'—O—$CH_2CH_2OCH_3$, also known as 2'-O-(2-methoxyethyl) or 2'-MOE] (Martin et al , *Helv. Chim. Acta*, 1995, 78, 486), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in co-owned U.S. patent application Ser. No. 09/016,520, filed on Jan. 30, 1998, the contents of which are herein incorporated by reference.

Other preferred modifications include 2'-methoxy (2'-O-$CH_3$), 2'-aminopropoxy (2'-$OCH_2CH_2CH_2NH_2$) and 2'-fluoro (2'-F) Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugars structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,0531 5,639,873; 5,646,265; 5,658,873; 5,670,633; and 5,700,920, each of which is herein incorporated by reference, and U.S. patent application Ser. No. 08/468,037, filed on Jun. 5, 1995, also herein incorporated by reference.

D. Other Modifications

Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a Lhiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717; 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

E. Chimeric Oligonucleotides

The present invention also includes antisense compounds which are chimeric compounds. "Chimeric" antisense compounds or "chimeras, " in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. RNase H-mediated target cleavage is distinct from the use of ribozymes to cleave nucleic acids, and ribozymes are not comprehended by the present invention.

By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for, or stability when duplexed with, the target RNA molecule but are unable to support nuclease activity (e.g., 2'-fluoro- or 2'-methoxyethoxy- substituted). Other chimeras include "hemimers," that is, oligonucleotides in which the 5' portion of the oligonucleotide serves as a substrate for, e.g., RNase H, whereas the 3' portion is modified in such a fashion so as to have greater affinity for, or stability when duplexed with, the target RNA molecule but is unable to support nuclease activity (e.g., 2'-fluoro- or 2'-methoxyethoxy- substituted), or vice-versa.

A number of chemical modifications to oligonucleotides that confer greater oligonucleotide:RNA duplex stability have been described by Freier et al. (*Nucl. Acids Res.*, 1997, 25, 4429). Such modifications are preferred for the RNase H-refractory portions of chimeric oligonucleotides and may generally be used to enhance the affinity of an antisense compound for a target RNA.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference, and U.S. patent application Ser. No. 08/465,880, filed on Jun. 6, 1995, also herein incorporated by reference.

F. Synthesis

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

1. Teachings regarding the synthesis of particular modified oligonucleotides may be found in the following U.S. patents or pending patent applications: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'—O—alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168, issued Jun. 29, 1993, and 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

2. Bioequivalents

The compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to "prodrugs" and "pharmaceutically acceptable salts" of the antisense compounds of the invention, pharmaceutically acceptable salts of such prodrugs, and other bioequivalents.

A. Oligonucleotide Prodrugs

The antisense compounds of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the antisense compounds of the invention are prepared as SATE [(S-acetyl-2-thioethyl) phosphate] derivatives according to the methods disclosed in WO 93/24510 to Gosselin et al., published Dec. 9, 1993.

B. Pharmaceutically Acceptable Salts

The term pharmaceutically acceptable salts, refers to physiologically and pharmaceutically acceptable salts of the antisense compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are chloroprocaine, choline, N,N'-dibenzylethylenediamine, diethanolamine, dicyclohexylamine, ethylenediamine, N-methylglucamine, and procaine (see, for example, Berge et al., "Pharmaceutical Salts," *J. of Pharma Sci.*, 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, embonic acid, 4-aminosalicylic acid, 2-phenoxybenzoic acid, nicotinic acid, isonicotinic acid or 2-acetoxybenzoic acid; and with amino acids, such as the 20 alpha-amino acids involved in the synthesis of proteins in nature, for example glutamic acid or aspartic acid, and also with naphthalene-1,5-disulfonic acid, phenylacetic acid, ethane-1,2-disulfonic acid, ethanesulfonic acid, methanesulfonic acid, 2-hydroxyethanesulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

3. Exemplary Utilities of the Invention

The oligonucleotides of the present invention specifically hybridize to nucleic acids (e.g., mRNAs) encoding a LFA-3 protein. The antisense compounds of the present invention can be utilized as therapeutic compounds, as diagnostic tools or research reagents that can be incorporated into kits as well as other methodologies as will be apparent to persons of ordinary skill in the art.

A. Assays and Diagnostic Applications

The oligonucleotides of the present invention can be used to detect the presence of LFA-3 protein-specific nucleic acids in a cell or tissue sample. For example, radiolabeled oligonucleotides can be prepared by $^{32}P$ labeling at the 5' end with polynucleotide kinase. (Sambrook et al., *Molecular Cloning. A Laboratory Manual*, Cold Spring Harbor Laboratory Press, 1989, Volume 2, pg. 10.59.) Radiolabeled oligonucleotides are then contacted with cell or tissue samples suspected of containing LFA-3 protein message RNAs (and thus LFA-3 proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of LFA-3 proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a LFA-3 protein gene. Quantitation of the silver grains permits detection of the expression of mRNA molecules encoding these proteins and permits targeting of oligonucleotides to these areas.

Analogous assays for fluorescent detection of expression of LFA-3 protein nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va. Other means of labeling oligonucleotides are known in the art (see, e.g., Ruth, Chapter 6 In: *Methods in Molecular Biology, Vol. 26: Protocols for Oligonucleotide Conjugates*, Agrawal, ed., Humana Press Inc., Totowa, N.J., 1994, pages 167–185).

Kits for detecting the presence or absence of expression of a LFA-3 protein may also be prepared. Such kits include an oligonucleotide targeted to an appropriate gene, i.e., a gene encoding a LFA-3 protein. Appropriate kit and assay formats, such as, e.g., "sandwich" assays, are known in the art and can easily be adapted for use with the antisense compounds of the invention. Hybridization of the antisense compounds of the invention with a nucleic acid encoding a LFA-3 protein can be detected by means known in the art. Such means may include conjugation of an enzyme to the oligonucleotide, radiolabelling of the oligonucleotide or any other suitable detection systems.

B. Biologically Active Oligonucleotides

The invention is also drawn to the administration of oligonucleotides having biological activity to cultured cells, isolated tissues and organs and animals. By "having biological activity," it is meant that the oligonucleotide functions to modulate the expression of one or more genes in cultured cells, isolated tissues or organs and/or animals. Such modulation can be achieved by an antisense oligonucleotide by a variety of mechanisms known in the art, including but not limited to transcriptional arrest; effects on RNA processing (capping, polyadenylation and splicing) and transportation; enhancement of cellular degradation of the target nucleic acid; and translational arrest (Crooke et al., *Exp. Opin. Ther. Patents*, 1996, 6:855).

In an animal other than a human, the compositions and methods of the invention can be used to study the function of one or more genes in the animal. For example, antisense oligonucleotides have been systemically administered to rats in order to study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., *Nature*, 1993, 363:260; Dean et al., *Proc. Natl. Acad. Sci. U.S.A.*, 1994, 91:11762; and Wahlestedt et al., *Science*, 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.*, 1994, 15:250).

The compositions and methods of the invention also have therapeutic uses in an animal, including a human, having (i.e., suffering from), or known to be or suspected of being prone to having, a disease or disorder that is treatable in whole or in part with one or more nucleic acids. The term "therapeutic uses" is intended to encompass prophylactic, palliative and curative uses wherein the antisense compounds of the invention are contacted with animal cells either in vivo or ex vivo. When contacted with animal cells ex vivo, a therapeutic use includes incorporating such cells into an animal after treatment with one or more of the antisense compounds of the invention.

For therapeutic uses, an animal suspected of having a disease or disorder which can be treated or prevented by modulating the expression or activity of a LFA-3 protein is, for example, treated by administering oligonucleotides in accordance with this invention. The antisense compounds of the invention can be utilized in pharmaceutical compositions by adding an effective amount of an oligonucleotide to a suitable pharmaceutically acceptable carrier such as, e.g., a diluent. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans. The following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections.

As used herein, the term "disease or disorder" (1) includes any abnormal condition of an organism or part, especially as a consequence of infection, inherent weakness, environmental stress, that impairs normal physiological functioning; (2) excludes pregnancy per se but not autoimmune and other diseases associated with pregnancy; and (3) includes cancers and tumors. The term "known to be or suspected of being prone to having a disease or disorder" indicates that the subject animal has been determined to be, or is suspected of being, at increased risk, relative to the general population of such animals, of developing a particular disease or disorder as herein defined. For example, a subject animal "known to be or suspected of being prone to having a disease or disorder" could have a personal and/or family medical history that includes frequent occurrences of a particular disease or disorder. As another example, a subject animal "known to be or suspected of being prone to having a disease or disorder" could have had such a susceptibility determined by genetic screening according to techniques known in the art (see, e.g., U.S. Congress, Office of Technology Assessment, Chapter 5 In: *Genetic Monitoring and Screening in the Workplace*, OTA-BA-455, U.S. Government Printing Office, Washington, D.C., 1990, pages 75–99). The term "a disease or disorder that is treatable in whole or in part with one or more antisense compounds" refers to a disease or disorder, as herein defined, (1) the management, modulation or treatment thereof, and/or (2) therapeutic, curative, palliative and/or prophylactic relief therefrom, can be provided via the administration of compositions comprising one or more antisense compounds of the invention.

4. Pharmaceutical Compositions Comprising Compounds of the Invention

The present invention provides for therapeutic and pharmaceutical compositions comprising one or more LFA-3-modulating antisense compounds. Compositions for the administration of the antisense compounds of the invention may include sterile aqueous solutions which may also contain buffers, diluents and other suitable additives.

A. Compositions for Alimentary Delivery

In a preferred embodiment of the invention, one or more LFA-3-modulating antisense compounds are administered via alimentary delivery, preferably by oral administration. Pharmaceutical compositions for oral administration include powders or granules, suspensions or solutions in water or non-aqueous media, capsules, sachets, troches, tablets or SECs (soft elastic capsules or "caplets"). Thickeners, flavoring agents, diluents, emulsifiers, dispersing aids, carrier substances or binders may be added to such compositions. Such pharmaceutical compositions have the effect of delivering the antisense compound(s) to the alimentary canal for exposure to the mucosa thereof. Accordingly, the pharmaceutical composition can comprise material effective in protecting the oligonucleotide from pH extremes of the stomach, or in releasing the oligonucleotide over time, to optimize the delivery thereof to a particular mucosal site. Enteric coatings for acid-resistant tablets, capsules and caplets are known in the art and typically include acetate phthalate, propylene glycol and sorbitan monoleate. Various methods for producing pharmaceutical compositions for alimentary delivery are well known in the art. See, generally, Nairn, Chapter 83; Block, Chapter 87; Rudnic et al., Chapter 89; Porter, Chapter 90; and Longer et al., Chapter 91 In: *Remington's Pharmaceutical Sciences*, 18th Ed., Gennaro, ed., Mack Publishing Co., Easton, Pa., 1990.

The antisense compounds of the invention can be incorporated in a known manner into customary pharmaceutical compositions, such as tablets, coated tablets, pills, granules, aerosols, syrups, emulsions, suspensions and solutions, using inert, non-toxic, pharmaceutically acceptable carriers (excipients). The therapeutically active compound should in each case be present here in a concentration of about 0.5% to about 95% by weight of the total mixture, i.e., in amounts which are sufficient to achieve the stated dosage range. The pharmaceutical compositions are prepared, for example, by diluting the active compounds with pharmaceutically acceptable carriers, if appropriate using emulsifying agents and/or dispersing agents, and, for example, in the case where water is used as the diluent, organic solvents can be used as auxiliary solvents if appropriate. Pharmaceutical compositions may be formulated in a conventional manner using additional pharmaceutically acceptable carriers as appropriate. Thus, the compositions may be prepared by conventional means with additional excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets are coated by methods well known in the art and may also contain flavoring, coloring and/or sweetening agents.

Compositions comprising one or more LFA-3-modulating antisense compounds can be administered via the rectal mode. In particular, therapeutic or pharmaceutical compositions for rectal administration include foams, solutions (enemas) and suppositories. Rectal suppositories for adults are usually tapered at one or both ends and typically weigh about 2 g each, with infant rectal suppositories typically weighing about one-half as much when the usual base, cocoa butter, is used (Block, Chapter 87 In: *Remington's Pharmaceutical Sciences*, 18th Ed., Gennaro, ed., Mack Publishing Co., Easton, Pa., 1990).

The pharmaceutical compositions, which may conveniently be presented in unit dosage form, may be prepared according to conventional techniques well known in the pharmaceutical industry. Such techniques include the step of bringing into association the active ingredient(s) with the pharmaceutically acceptable carrier(s). In general the pharmaceutical compositions are prepared by uniformly and intimately bringing into association the active ingredient(s) with liquid excipients or finely divided solid excipients or both, and then, if necessary, shaping the product.

Pharmaceutical compositions of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein. Sustained release oral delivery systems and/or enteric coatings for orally administered dosage forms are described in U.S. Pat. Nos. 4,704,295; 4,556,552; 4,309,406; and 4,309,404.

B. Additives

Pharmaceutical and therapeutic compositions comprising one or more of the antisense compounds of the invention may further include sterile aqueous solutions which may also contain buffers, diluents and other suitable additives. Pharmaceutically acceptable organic or inorganic carrier substances suitable for non-parenteral administration which do not deleteriously react with the antisense compounds can be used. The pharmaceutical compositions can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with the oligonucleotide(s) of the pharmaceutical composition. Pharmaceutical compositions in the form of aqueous suspensions may contain substances which increase the viscosity of the suspension including, for example, sodium carboxymethylcellulose, sorbitol and/or dextran. Optionally, such compositions may also contain one or more stabilizers, penetration enhancers, carrier compounds or pharmaceutically acceptable carriers.

(1) Penetration Enhancers

Pharmaceutical compositions comprising the oligonucleotides of the present invention may also include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., *Critical Reviews in Therapeutic Drug Carrier Systems*, 1991, 8:91–192; Muranishi, *Critical Reviews in Therapeutic Drug Carrier Systems*, 1990, 7:1).

Fatty Acids

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arichidonic 15 acid, glyceryl 1-monocaprate, acylcarnitines, acylcholines, 1-dodecylazacycloheptan-2-one, mono- and di-glycerides and physiologically acceptable salts thereof (i. e., oleate, laurate, caprate, myristate, palmitate, stearate, linoleate, etc.) (Lee et al., *Critical Reviews in Therapeutic Drug Carrier Systems*, 1991, page 92; Muranishi, *Critical Reviews in Therapeutic Drug Carrier Systems*, 1990, 7:1; El-Hariri et al., *J. Pharm. Pharmacol.*, 1992, 44:651).

Bile Salts

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, "bile salt" includes any of the naturally occurring components of bile and any of their synthetic derivatives.

Chelating Agents

Chelating agents have the added advantage of also serving as DNase inhibitors and include, but are not limited to, citric acid, disodium ethylenediaminetetraacetate (EDTA), salicylates (e.g., sodium salicylate, 5-methoxysalicylate and homovanilate), N-acyl derivatives of collagen, laureth-9 and N-amino acyl derivatives of beta-diketones (enamines) (Lee et al., *Crit. Rev. Therap. Drug Carrier Systems*, 1991, p. 92; Muranishi, *Crit. Rev. Therap. Drug Carrier Systems*, 1990, 7, 1; Buur et al., *J. Control Rel.*, 1990, 14, 43).

Surfactants

Surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, page 92); and perfluorochemical emulsions, such as FC-43 (Takahashi et al., *J. Pharm. Phamacol.*, 1988, 40:252).

Non-Surfactants

Non-surfactants include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39:621).

(2) Carrier Compounds

As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.*, 1995, 5:115; Takakura et al., *Antisense & Nucl. Acid Drug Dev.*, 1996, 6:177).

(3) Pharmaceutically Acceptable Carriers

In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e. g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Suitable pharmaceutically acceptable carriers include, but are not limited to, water, salt solutions, alcohol, polyethylene glycols, gelatin, lactose, amylose, magnesium stearate, talc, silicic acid, hydroxymethylcellulose, polyvinylpyrrolidone viscous paraffin and the like.

(4) Miscellaneous Additional Components

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

C. Colloidal Dispersion Systems

Regardless of the method by which the antisense compounds of the invention are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, lipid: oligonucleotide complexes of uncharacterized structure and liposomes.

A preferred colloidal dispersion system is a plurality of liposomes. Liposomes are microscopic spheres having an aqueous core surrounded by one or more outer layer(s) made up of lipids arranged in a bilayer configuration (see, generally, Chonn et al., *Current Op. Biotech.*, 1995, 6, 698). The therapeutic potential of liposomes as drug delivery agents was recognized nearly thirty years ago (Sessa et al., *J. Lipid Res.*, 1968, 9, 310). Liposomes, in some instances, may be used as cellular delivery vehicles for bioactive agents in vitro and in vivo (Mannino et al., *Biotechniques*, 1988, 6, 682; Blume et al., *Biochem. et Biophys. Acta*, 1990, 1029, 91; Lappalainen et al., *Antiviral Res.*, 1994, 23, 119. For example, it has been shown that large unilamellar vesicles (LUV), which range in size from 0.2–0.4 microns, can encapsulate a substantial percentage of an aqueous buffer containing large macromolecules. RNA, DNA and intact virions can be encapsulated within the aqueous interior and delivered to brain cells in a biologically active form (Fraley et al., *Trends Biochem. Sci.*, 1981, 6, 77).

The targeting of colloidal dispersion systems, including liposomes, can be either passive or active. Passive targeting utilizes the natural tendency of liposomes to distribute to cells of the reticuloendothelial system in organs that contain sinusoidal capillaries. Active targeting, by contrast, involves modification of the liposome by coupling thereto a specific ligand such as a viral protein coat (Morishita et al., *Proc. Natl. Acad. Sci. (U.S.A.)*, 1993, 90, 8474), monoclonal antibody (or a suitable binding portion thereof), sugar, glycolipid or protein (or a suitable oligopeptide fragment thereof), or by changing the composition and/or size of the liposome in order to achieve distribution to organs and cell types other than the naturally occurring sites of localization.

The surface of the targeted colloidal dispersion system can be modified in a variety of ways. In the case of a liposomal targeted delivery system, lipid groups can be incorporated into the lipid bilayer of the liposome in order to maintain the targeting ligand in close association with the lipid bilayer. Various linking groups can be used for joining the lipid chains to the targeting ligand. The targeting ligand, which binds a specific cell surface molecule found predominantly on cells to which delivery of the compounds of the invention is desired, may be, for example, (1) a hormone, growth factor or a suitable oligopeptide fragment thereof which is bound by a specific cellular receptor predominantly expressed by cells to which delivery is desired or (2) a polyclonal or monoclonal antibody, or a suitable fragment thereof (e.g., Fab; F(ab')$_2$) which specifically binds an antigenic epitope found predominantly on targeted cells. Two or more bioactive agents (e.g., an antisense oligonucleotide and a conventional drug; two oligonucleotides) can be combined within, and delivered by, a single liposome. It is also possible to add agents to colloidal dispersion systems which enhance the intercellular stability and/or targeting of the contents thereof.

The liposomes of the invention are formed from vesicle-forming lipids which generally include one or more neutral or negatively charged phospholipids, preferably one or more neutral phospholipids, usually in combination with one or more sterols, particularly cholesterol. Examples of lipids useful in liposome production include phosphatidyl compounds, such as phosphatidylglycerol, phosphatidylcholine, phosphatidylserine, sphingolipids, phosphatidylethanolamine, cerebrosides and gangliosides. Typically, the major lipid component of the liposomes is a phosphatidylcholine (PC) or PC derivative. PC derivatives with a variety of acyl chain groups of varying chain length and degree of saturation are commercially available or may be synthesized by known techniques. For purposes of filter sterilization, less-saturated PCs are generally more easily sized, particularly when the liposomes must be sized below about 0.3 microns. PCs containing saturated fatty acids with carbon chain lengths in the range of $C_{14}$ to $C_{22}$, particularly $C_{16}$ to $C_{18}$, are preferred, particularly diacyl phosphatidylglycerols. Illustrative phospholipids include, for example, dipalmitoylphosphatidylcholine, phosphatidylcholine and distearoylphosphatidylcholine. Phosphatidylcholines with mono- and di-unsaturated fatty acids and mixtures of saturated and unsaturated fatty acids may also be used. Other suitable phospholipids include those with head groups other than choline, such as, for example, ethanolamine, serine, glycerol and inositol. Other suitable lipids include phosphonolipids in which the fatty acids are linked to glycerol via ether linkages rather than ester linkages. Preferred liposomes will include a sterol, e.g., cholesterol, at molar ratios of from about 0.1 to 1.0 (sterol: phospholipid).

Typically, the liposomes of the invention will contain, in their aqueous interiors, one or more antisense oligonucleotides in an amount of from about 0.005 ng/mL to about 400 mg/mL, preferably from about 0.01 ng/mL to about 200 mg/mL, most preferably from about 0.1 ng/mL to about 100 mg/mL, where "about" indicates ±5% of the desired concentration.

Compositions of the invention may include one or more antisense compounds and/or other therapeutic agents entrapped within sterically stabilized liposomes. As used herein, the term "sterically stabilized liposome" refers to a liposome comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (Allen et al., *FEBS Letts.*, 1987, 223, 42; Wu et al., *Cancer Res.*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Letters*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Letts.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. 0,445,131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0,496,813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and 5,556,948 (Tagawa et al.) describe PEG-containing liposomes that can be further derivatized via functional surface moieties.

A limited number of liposomes comprising nucleic acids are known in the art. Published PCT application No. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene. WO 97/46671 to Klimuk et al. discloses liposomes comprising antisense oligonucleotides targeted to genes encoding ICAM-1. One or more antisense compounds of the invention can be formulated in a [lipid: (antisense compound)] complex comprising one or more cationic lipids as disclosed in U.S. Pat. No. 5,705,385 to Bally et al. and in WO 96/40964 to Wheeler et al., or in lipoprotein-containing complexes such as are described in WO 98/00556 to Kim et al.

The liposomes of the invention can be prepared by any of a variety of known techniques. For example, the liposomes can be formed by any conventional technique for preparing multilamellar lipid vesicles (MLVs), i.e., by depositing one or more selected lipids on the inside wall of a suitable vessel by dissolving the lipid in chloroform, evaporating the chloroform and then adding an aqueous solution which comprises the agent(s) to be encapsulated to the vessel, allowing the aqueous solution to hydrate the lipid, and swirling or vortexing the resulting lipid suspension. This process yields a mixture including the desired liposomes.

As another example, techniques used for producing large unilamellar vesicles (LUVs), such as, e.g., reverse-phase evaporation, infusion procedures and detergent dilution, can be used to produce the liposomes. These and other methods for producing lipid vesicles are described in *Liposome Technology, Volume I* (Gregoriadis, Ed., CRC Press, Boca Raton, Fla., 1984). The liposomes can be in the form of steroidal lipid vesicles, stable plurilamellar vesicles (SPLVs), monophasic vesicles (MPVs) or lipid matrix carriers (LMCs) of the type disclosed in U.S. Pat. Nos. 4,588,578 and 4,610,868 (both to Fountain et al.), 4,522,803 (to Lenk et al.), and 5,008,050 (to Cullis et al.). In the case of MLVs, the liposomes can be subjected to multiple (five or more) freeze-thaw cycles to enhance their trapped volumes and trapping efficiencies and to provide a more uniform interlamellar distribution of solute if desired (Mayer et al.,*J. Biol. Chem.*, 1985, 260, 802). Specific methods for making particular oligodeoxynucleotide:liposome compositions are described in U.S. Pat. No. 5,665,710 to Rahman et al.

Following their preparation, liposomes may be sized to achieve a desired size range and relatively narrow distribution of sized particles. In preferred embodiments, the liposomes have a lower range of diameters of from about 50 to about 75 nM, most preferably about 60 nM, and an upper range of diameters from about 75 to about 150 nM, most preferably about 125 nM, where "about" indicates +10 nM.

Several techniques are available for sizing liposomes to a desired size range. Sonicating a liposome suspension by either bath or probe sonication produces a progressive size reduction down to small unilamellar vesicles (SUVs) less than about 0.05 microns in size. Homogenization, which relies on shearing energy to fragment large liposomes into smaller ones, is another known sizing technique in which MLVs are recirculated through a standard emulsion homogenizer until a selected liposome size range, typically between about 0.1 and about 0.5 microns, is achieved. Extrusion of liposomes through a filter or membrane is another method for producing liposomes having a desired size range (see, for example, U.S. Pat. No. 4,737,323 to Martin et al. and 5,008,050 to Cullis et al.). Other useful sizing methods are known to those skilled in the art. In most such methods, the particle size distribution can be monitored by conventional laser-beam size determination or other means known in the art.

Liposomes may be dehydrated, preferably under reduced pressure using standard freeze-drying equipment, for extended storage. Whether dehydrated or not, the liposomes and their surrounding media can first be frozen in liquid nitrogen and placed under reduced pressure. Although the addition of the latter freezing step makes for a longer overall dehydration process, there is less damage to the lipid vesicles, and less loss of their internal contents, when the liposomes are frozen before dehydration.

To ensure that the a significant portion of the liposomes will endure the dehydration process intact, one or more protective sugars may be made available to interact with the lipid vesicle membranes and keep them intact as water is removed. Appropriate sugars include, but are not limited to, trehalose, maltose, sucrose, lactose, glucose, dextran and the like. In general, disaccharide sugars may work better than monosaccharide sugars, with trehalose and sucrose being particularly effective in most cases, but other, more complicated sugars may alternatively be used. The amount of sugar to be used depends on the type of sugar and the characteristics of the lipid vesicles. Persons skilled in the art can readily test various sugars and concentrations to determine what conditions work best for a particular lipid vesicle preparation (see, generally, Harrigan et al., *Chem. Phys. Lipids*, 1990, 52, 139, and U.S. Pat. No. 4,880,635 to Janoff et al. ). Generally, sugar concentrations of greater than or equal to about 100 mM have been found to result in the desired degree of protection. Once the liposomes have been dehydrated, they can be stored for extended periods of time until they are to be used. The appropriate conditions for storage will depend on the chemical composition of the lipid vesicles and their encapsulated active agent(s). For example, liposomes comprising heat labile agents should be stored under refrigerated conditions so that the potency of the active agent is not lost.

Two or more bioactive agents (e.g., an oligonucleotide and a conventional drug, or two or more oligonucleotides; see below) can be combined within, and delivered by, a single liposome. It is also possible to add agents to colloidal dispersion systems which enhance the intercellular stability and/or targeting of the contents thereof.

5. Methods of Administration of Compounds of the Invention

The administration of therapeutic or pharmaceutical compositions comprising the antisense compounds of the invention is believed to be within the skill of those in the art. In general, a patient in need of therapy or prophylaxis is administered a composition comprising one or more antisense compounds in accordance with the invention, commonly in a pharmaceutically acceptable carrier, in doses ranging from 0.01 $\mu$g to 100 g per kg of body weight depending on the age of the patient and the severity of the disorder or disease state being treated. Dosing is dependent on severity and responsiveness of the disease state to be treated, with the course of treatment lasting from several days to several months, or until a cure is effected or a diminution or prevention of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual antisense compounds, and can generally be estimated based on $EC_{50}$s found to be effective in in vitro and in vivo animal models.

A. Treatment Regimens

In the context of the invention, the term "treatment regimen" is meant to encompass therapeutic, palliative and prophylactic modalities of administration of one or more compositions comprising one or more antisense compounds of the invention. A particular treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

An optimal dosing schedule is used to deliver a therapeutically effective amount of the oligonucleotide being administered via a particular mode of administration. The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs may vary, determination of optimal ranges for effective amounts of pharmaceutical compositions is within the skill of the art. Human doses can be extrapolated from animal studies (Katocs et al., Chapter 27 In: *Remington's Pharmaceutical Sciences*, 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: *Goodman & Gilman's The Pharmacological Basis of Therapeutics*, 9th Ed., Hardman et al., eds., McGraw-Hill, New York, N.Y., 1996).

Following successful treatment, it may be desirable to have the patient undergo maintenance therapy to prevent the recurrence of the disease state, wherein the nucleic acid is administered in maintenance doses, ranging from 0.01 ug to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 ug to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

In another method of the invention, a first antisense oligonucleotide targeted to a first LFA-3 protein is used in combination with a second antisense oligonucleotide targeted to a second LFA-3 protein in order to modulate such LFA-3 proteins to a more extensive degree than can be achieved when either oligonucleotide is used individually. In various embodiments of the invention, the first and second LFA-3 proteins which are targeted by such oligonucleotides are identical, are different LFA-3 proteins or are different isoforms of the same LFA-3 protein.

In some cases it may be more effective to treat a patient with a composition comprising one or more antisense compounds of the invention in conjunction with other, traditional therapeutic modalities in order to increase the efficacy of a treatment regimen. In the context of the invention, the term "treatment regimen" is meant to encompass therapeutic, palliative and prophylactic modalities. Following treatment, the patient is monitored for changes in his/her condition and for alleviation of the symptoms of the disorder or disease state. The dosage of the therapeutic or pharmaceutical composition may either be increased in the event the patient does not respond significantly to current dosage levels, or the dose may be decreased if an alleviation of the symptoms of the disorder or disease state is observed, or if the disorder or disease state has been ablated.

Prophylactic modalities for high risk individuals are also encompassed by the invention. As used herein, the term "high risk individual" is meant to refer to an individual for whom it has been determined, via, e.g., individual or family history or genetic testing, that there is a significantly higher than normal probability of being susceptible to the onset or recurrence of a disease or disorder. As part of a treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compared to the effect observed when a second pharmaceutical composition lacking the active agent is administered to a similarly situated individual. The therapeutic and pharmaceutical compositions of the present invention may be administered in a number of ways depending upon whether local or systemic treatment is desired and upon the area to be treated. Typically, either oral or parenteral administration is employed.

B. Parenteral Delivery

The term "parenteral delivery" refers to the administration of one or more antisense compounds of the invention to an animal in a manner other than through the digestive canal. Parenteral administration includes intravenous (i.v.) drip, subcutaneous, intraperitoneal (i.p.) or intramuscular injection, or intrathecal or intraventricular administration. Compositions for parenteral, intrathecal or intraventricular administration may include sterile aqueous solutions which may also contain buffers, diluents and other suitable additives. Means of preparing and administering parenteral pharmaceutical compositions are known in the art (see, e.g., Avis, Chapter 84 In: *Remington's Pharmaceutical Sciences*, 18th Ed., Gennaro, ed., Mack Publishing Co., Easton, Pa., 1990, pages 1545–1569). Parenteral means of delivery include, but are not limited to, the following illustrative examples.

Intravitreal injection, for the direct delivery of drug to the vitreous humor of a mammalian eye, is described in U.S. Pat. No. 5,591,720, the contents of which are hereby incorporated by reference. Means of preparing and administering ophthalmic preparations are known in the art (see, e.g., Mullins et al., Chapter 86 In: *Remington's Pharmaceutical Sciences*, 18th Ed., Gennaro, ed., Mack Publishing Co., Easton, Pa., 1990, pages 1581–1595).

Intravenous administration of antisense oligonucleotides to various non-human mammals has been described by Iversen (Chapter 26 In: *Antisense Research and Applications*, Crooke et al., eds., CRC Press, Boca Raton, Fla., 1993, pages 461–469). Systemic delivery of oligonucleotides to non-human mammals via intraperitoneal means has also been described (Dean et al., *Proc. Natl. Acad. Sci. U.S.A.*, 1994, 91, 11766).

Intraluminal drug administration, for the direct delivery of drug to an isolated portion of a tubular organ or tissue (e.g., such as an artery, vein, ureter or urethra), may be desired for the treatment of patients with diseases or conditions afflicting the lumen of such organs or tissues. To effect this mode of oligonucleotide administration, a catheter or cannula is surgically introduced by appropriate means. For example, for treatment of the left common carotid artery, a cannula is inserted thereinto via the external carotid artery. After isolation of a portion of the tubular organ or tissue for which treatment is sought, a composition comprising the antisense compounds of the invention is infused through the cannula or catheter into the isolated segment. After incubation for from about 1 to about 120 minutes, during which the oligonucleotide is taken up by cells of the interior lumen of the vessel, the infusion cannula or catheter is removed and flow within the tubular organ or tissue is restored by removal of the ligatures which effected the isolation of a segment thereof (Morishita et al., *Proc. Natl. Acad. Sci. U.S.A.*, 1993, 90, 8474). Antisense oligonucleotides may also be combined with a biocompatible matrix, such as a hydrogel material, and applied directly to vascular tissue in vivo (Rosenberg et al., U.S. Pat. No. 5,593,974, issued Jan. 14, 1997).

Intraventricular drug administration, for the direct delivery of drug to the brain of a patient, may be desired for the treatment of patients with diseases or conditions afflicting the brain. To effect this mode of oligonucleotide administration, a silicon catheter is surgically introduced into a ventricle of the brain of a human patient, and is connected to a subcutaneous infusion pump (Medtronic Inc., Minneapolis, Minn.) that has been surgically implanted in the abdominal region (Zimm et al., *Cancer Research*, 1984, 44, 1698; Shaw, *Cancer*, 1993, 72(11 Suppl., 3416). The pump is used to inject the oligonucleotides and allows precise dosage adjustments and variation in dosage schedules with the aid of an external programming device. The reservoir capacity of the pump is 18–20 mL and infusion rates may range from 0.1 mL/h to 1 mL/h. Depending on the frequency of administration, ranging from daily to monthly, and the dose of drug to be administered, ranging from 0.01 ug to 100 g per kg of body weight, the pump reservoir may be refilled at 3–10 week intervals. Refilling of the pump is accomplished by percutaneous puncture of the pump's self-sealing septum.

Intrathecal drug administration, for the introduction of a drug into the spinal column of a patient may be desired for the treatment of patients with diseases of the central nervous system (CNS). To effect this route of oligonucleotide administration, a silicon catheter is surgically implanted into the L3-4 lumbar spinal interspace of a human patient, and is connected to a subcutaneous infusion pump which has been surgically implanted in the upper abdominal region (Luer and Hatton, *The Annals of Pharmacotherapy*, 1993, 27, 912, 1993; Ettinger et al. *Cancer*, 1978, 41, 1270; Yaida et al., *Regul. Pept.*, 1985, 59, 193). The pump is used to inject the oligonucleotides and allows precise dosage adjustments and variations in dose schedules with the aid of an external programming device. The reservoir capacity of the pump is 18–20 mL, and infusion rates may vary from 0.1 mL/h to 1 mL/h. Depending on the frequency of drug administration, ranging from daily to monthly, and dosage of drug to be administered, ranging from 0.01 ug to 100 g per kg of body weight, the pump reservoir may be refilled at 3–10 week intervals. Refilling of the pump is accomplished by a single percutaneous puncture to the self-sealing septum of the pump. The distribution, stability and pharmacokinetics of oligonucleotides within the CNS are followed according to known methods (Whitesell et al., *Proc. Natl. Acad. Sci. U.S.A.*, 1993, 90, 4665).

To effect delivery of oligonucleotides to areas other than the brain or spinal column via this method, the silicon catheter is configured to connect the subcutaneous infusion pump to, e.g., the hepatic artery, for delivery to the liver (Kemeny et al., *Cancer*, 1993, 71, 1964). Infusion pumps may also be used to effect systemic delivery of oligonucleotides (Ewel et al., *Cancer Res.*, 1992, 52, 3005; Rubenstein et al., *J. Surg. Oncol.*, 1996, 62, 194).

Epidermal and Transdermal Delivery, in which pharmaceutical compositions containing drugs are applied topically, can be used to administer drugs to be absorbed by the local dermis or for further penetration and absorption by underlying tissues, respectively. Means of preparing and administering medications topically are known in the art (see, e.g., Block, Chapter 87 In: *Remington's Pharmaceutical Sciences*, 18th Ed., Gennaro, ed., Mack Publishing Co., Easton, Pa., 1990, pages 1596–1609).

Vaginal Delivery provides local treatment and avoids first pass metabolism, degradation by digestive enzymes, and potential systemic side-effects. This mode of administration may be preferred for antisense oligonucleotides targeted to pathogenic organisms for which the vagina is the usual habitat, e.g., *Trichomonas vaginalis*. In another embodiment, antisense oligonucleotides to genes encoding sperm-specific antibodies can be delivered by this mode of administration in order to increase the probability of conception and subsequent pregnancy. Vaginal suppositories (Block, Chapter 87 In: *Remington's Pharmaceutical Sciences*, 18th Ed., Gennaro, ed., Mack Publishing Co., Easton, Pa., 1990, pages 1609–1614) or topical ointments can be used to effect this mode of delivery.

Intravesical Delivery provides local treatment and avoids first pass metabolism, degradation by digestive enzymes, and potential systemic side-effects. However, the method requires urethral catheterization of the patient and a skilled staff. Nevertheless, this mode of administration may be preferred for antisense oligonucleotides targeted to pathogenic organisms, such as *T. vaginalis*, which may invade the urogenital tract.

C. Alimentary Delivery

The term "alimentary delivery" refers to the administration, directly or otherwise, to a portion of the alimentary canal of an animal, of a composition comprising one or more of the antisense compounds of the invention. The term "alimentary canal" refers to the tubular passage in an animal that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastro-intestinal tract. Thus, the term "alimentary delivery" encompasses several routes of administration including, but not limited to, oral, rectal, endoscopic and sublingual/buccal administration. Compositions for alimentary delivery may include sterile aqueous solutions which may also contain buffers, diluents and other suitable additives. Means of preparing and administering oral pharmaceutical compositions are known in the art (see, e.g., Block, Chapter 87; Rudnic, Chapter 89; Porter, Chapter 90; and Longer, Chapter 91, In: *Remington's Pharmaceutical Sciences*, 18th Ed., Gennaro, ed., Mack Publishing Co., Easton, Pa., 1990, pages 1596–1614, 1633–1665, 1666–1675 and 1676–1693, respectively). Preferred compositions for the alimentary delivery of the antisense compounds of the invention are described in co-pending U.S. patent application Ser. No. 08/886,829 to Teng et al., filed Jul. 1, 1997, the entire disclosure of which is hereby incorporated by reference.

Buccal/Sublingual Administration

Delivery of a drug via the oral mucosa has several desirable features, including, in many instances, a more rapid rise in plasma concentration of the drug than via oral delivery (Harvey, Chapter 35 In: *Remington's Pharmaceutical Sciences*, 18th Ed., Gennaro, ed., Mack Publishing Co., Easton, Pa., 1990, page 711). Furthermore, because venous drainage from the mouth is to the superior vena cava, this route also bypasses rapid first-pass metabolism by the liver. Both features contribute to the sublingual route being the mode of choice for nitroglycerin (Benet et al., Chapter 1 In: *Goodman & Gilman's The Pharmacological Basis of Therapeutics*, 9th Ed., Hardman et al., eds., McGraw-Hill, New York, N.Y., 1996, page 7).

Endoscopic Administration

Endoscopy can be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho*, 1992, 19(10 Suppl.), 1591). Pharmaceutical compositions, including liposomal formulations, can be delivered directly into portions of the alimentary canal, such as, e.g., the duodenum (Somogyi et al., *Pharm. Res.*, 1995, 12, 149) or the gastric submucosa (Akamo et al., *Japanese J. Cancer Res.*, 1994, 85, 652) via endoscopic means. Gastric lavage devices (Inoue et al., *Artif. Organs*, 1997, 21, 28) and percutaneous endoscopic feeding devices (Pennington et al., *Aliment. Pharmacol. Ther.*, 1995, 9, 471) can also be used for direct alimentary delivery of pharmaceutical compositions.

Rectal Administration

Drugs administered by the oral route can often be alternatively administered by the lower enteral route, i.e., through the anal portal into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration may result in more prompt and higher blood levels than the oral route, but the converse may be true as well (Harvey, Chapter 35 In: *Remington's Pharmaceutical Sciences*, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass pass metabolism (Benet et al., Chapter 1 In: *Goodman & Gilman's The Pharmacological Basis of Therapeutics*, 9th Ed., Hardman et al., eds., McGraw-Hill, New York, N.Y., 1996).

Oral Administration

The preferred method of administration is oral delivery, which is typically the most convenient route for access to the systemic circulation. Absorption from the alimentary canal is governed by factors that are generally applicable, e.g., surface area for absorption, blood flow to the site of absorption, the physical state of the drug and its concentration at the site of absorption (Benet et al., Chapter 1 In: *Goodman & Gilman's The Pharmacological Basis of Therapeutics*, 9th Ed., Hardman et al., eds., McGraw-Hill, New York, N.Y., 1996, pages 5–7). Orally administered compositions comprising certain oligonucleotides are known in the art (see, for example, U.S. Pat. No. 5,591,721 to Agrawal et al.). Preferred compositions for the oral delivery of the antisense compounds of the invention are described in co-pending U.S. patent application Ser. No. 08/886,829 to Teng et al., filed Jul. 1, 1997, incorporated herein by reference.

Preferred compositions for the oral delivery of the antisense compounds of the invention are described in co-pending U.S. patent application Ser. No. 08/886,829 to Teng et al., filed Jul. 1, 1997, incorporated herein by reference.

EXAMPLES

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

Example 1

Synthesis of Oligonucleotides

A. General Synthetic Techniques

Oligonucleotides were synthesized on an automated DNA synthesizer using standard phosphoramidite chemistry with oxidation using iodine. β-Cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages.

The synthesis of 2'-O-methyl- (a.k.a. 2'-methoxy-) phosphorothioate oligonucleotides is according to the procedures set forth above substituting 2'-O-methyl β-cyanoethyldiisopropylphosphoramidites (Chemgenes, Needham, Mass.) for standard phosphoramidites and increasing the wait cycle after the pulse delivery of tetrazole and base to 360 seconds.

Similarly, 2'-O-propyl- (a.k.a 2' propoxy-) phosphorothioate oligonucleotides are prepared by slight modifications of this procedure and essentially according to procedures disclosed in U.S. patent application Ser. No. 08/383,666, filed Feb. 3, 1995.

The 2'-fluoro-phosphorothioate antisense compounds of the invention are synthesized using 5'-dimethoxytrityl-3'-phosphoramidites and prepared as disclosed in U.S. patent application Ser. No. 08/383,666, filed Feb. 3, 1995, and U.S. Pat. No. 5,459,255, which issued Oct. 8, 1996. The 2'-fluoro-oligonucleotides were prepared using phosphoramidite chemistry and a slight modification of the standard DNA synthesis protocol (i.e., deprotection was effected using methanolic ammonia at room temperature).

The 2'-methoxyethyl oligonucleotides were synthesized essentially according to the methods of Martin et al. (Helv. Chim. Acta, 1995, 78, 486). For ease of synthesis, the 3'-nucleotide of the 2'-methoxyethyl oligonucleotides was a deoxynucleotide, and 2'—O—$CH_2CH_2OCH_3$cytosines were 5-methyl cytosines, which were synthesized according to the procedures described below.

PNA antisense analogs are prepared essentially as described in U.S. Pat. Nos. 5,539,082 and 5,539,083, both of which issued Jul. 23, 1996.

B. 5-Methyl-2'-Methoxyethoxy-Cytosine

Oligonucleotides having 5-methyl-2'-methoxyethoxy-cytosine residues are prepared as follows.

(i) 2,2'-Anhydro[1-(β-D-arabinofuranosyl)-5-methyluridine]: 5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

(ii) 2'-O-Methoxyethyl-5-methyluridine: 2,2'-Anhydro-5-methyluridine (195, 0.81 M), tris(2-methoxyethyl)borate (231 g, 0.98 M) and 2 methoxyethanol (1.2 L) were added to a 2 L stainless steel pressure vessel and placed in a pre-heated oil bath at 160° C. After heating for 48 hours at 155–160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

(iii) 2'-O-Methoxyethyl-5'-O-dimethoxytrityl-5-methyluridine: 2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Mexane/Acetone (5:5:1) containing 0.5% $Et_3NH$. The pure fractions were evaporated to give 164 g of product. Approximately 20 g additional was obtained from the impure fractions to give a total yield of 183 g (57%).

(iv) 3'-O-Acetyl-2'-O-methoxyethyl-5'-O-dimethoxytrityl-5-methyluridine: 2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in CHCl (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approximately 90% product). The residue was purified on a 3.5 kg silica gel column and eluted using EtOAc/Hexane (4:1). Pure product fractions were evaporated to yield 96 g (84%).

(v) 3'-O-Acetyl-2'-O-methoxyethyl-5'-O-dimethoxytrityl-5-methyl-4-triazoleuridine: A first solution was prepared by dissolving 3'-O-acetyl-2'-o-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

(vi) 2'-O-Methoxyethyl-5'-O-dimethoxytrityl-5-methylcytidine: A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. Methanol (400 mL) saturated with $NH_3$ gas was added and the vessel heated to 100° C. for 2 hours (thin layer chromatography, tlc, showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

(vii) $N^4$-Benzoyl-2'-O-methoxyethyl-5'-O-dimethoxytrityl-5-methylcytidine: 2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g) The residue was chromatographed on a 1.5 kg silica column using EtOAc/Hexane (1:1) containing 0.5% $Et_3NH$ as the eluting solvent. The pure product fractions were evaporated to give 90 g (90%) of the title compound.

(viii) $N^4$-Benzoyl-2'-O-methoxyethyl-5'-O-dimethoxytrityl-5-methylcytidine-3'-amidite: N-Benzoyl-2'-O-methoxyethyl-5'-O-dimethoxytrityl -5-methylcytidine (74 g, 0.10 M) was dissolved in $CH_2Cl_2$ (1 L). Tetrazole diisopropylamine (7.1 g) and 2-cyanoethoxy-tetra (isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc/Hexane (3:1) as the eluting solvent. The pure fractions were combined to give 90.6 g (87%) of the title compound.

C. Purification

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and their phosphorothioate analogs were judged from electrophoresis to be greater than 80% full length material.

Example 2

Nucleotide Sequences of Oligonucleotides Targeted to LFA-3

A. Oligonucleotides Targeted to Nucleic Acids Encoding Human LFA-3

Table 1 lists the nucleotide sequences of a set of oligonucleotides designed to specifically hybridize to human LFA-3 mRNAs and their corresponding ISIS and SEQ ID numbers. The nucleotide co-ordinates of the target gene and gene target regions are also included. The nucleotide co-ordinates are derived from GenBank Accession No. Y00636, locus name "HSLFA3" (see also FIG. 2 of Wallner et al., *J. Exp. Med.*, 1987, 166, 923). The abbreviations for gene target regions are as follows: 5'-UTR, 5' untranslated region; AUG, translation initiation region; ORF, open reading frame; stop, translation termination region; 3'-UTR, 3' untranslated region. The location of the target sequences complementary to those of the oligonucleotides is shown in FIG. 1.

The nucleotides of the oligonucleotides whose sequences are presented in Table 1 are connected by phosphorothioate linkages, with the exception of ISIS 17159 which contains both phosphorothioate and phosphodiester linkages. These oligonucleotides are gapmers having, at both the 5' and 3' termini, five contiguous nucleotides modified at the 2' position (2'-methoxyethoxy). Internal nucleotides within these "gapmers" are unmodified at the 2' position (2'-deoxy).

TABLE 1

Nucleotide Sequences of Human LFA-3 oligonucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 16371 | CsCsCsGsCsGsTsCsGsCsTsCsCsCsAsGsCsAsAsCsC | 2 | 0012–0031 | AUG |
| 16372 | GsGsCsAsGsAsCsCsAsCsGsCsTsGsAsGsGsAsCsC | 3 | 0045–0064 | ORF |
| 16373 | AsAsGsGsCsAsCsAsTsTsGsCsTsTsGsGsTsAsCsA | 4 | 0141–0160 | ORF |
| 16374 | TsGsAsGsGsCsTsAsCsCsTsGsAsCsAsCsAsGsTsG | 5 | 0261–0280 | ORF |
| 16375 | AsTsTsGsGsAsGsTsTsGsGsTsTsCsTsGsTsCsTsG | 6 | 0740–0759 | ORF |
| 16376 | TsCsAsTsCsTsTsCsTsGsTsAsCsCsAsAsTsCsA | 7 | 0760–0779 | stop |
| 16377 | AsAsTsTsAsGsTsTsAsTsGsCsTsGsTsGsTsC | 8 | 0781–0800 | 3'-UTR |
| 16378 | TsAsCsAsTsTsTsCsCsAsAsCsAsGsTsTsGsTsTsC | 9 | 0853–0872 | 3'-UTR |
| 16379 | TsGsCsTsTsGsTsTsCsTsTsTsGsTsTsAsGsTsGsG | 10 | 0903–0922 | 3'-UTR |
| 16380 | AsTsAsAsTsAsAsGsTsTsGsAsTsGsAsCsAsGsCsC | 11 | 0931–0950 | 3'-UTR |
| 16381 | AsAsGsCsAsAsGsCsAsCsCsTsAsGsTsCsAsTsAsT | 12 | 0949–0968 | 3'-UTR |
| 16909 | TsGsAsGsGsCsTsAsCsCsTsGsAsCsAsCsAsGsTsG | 5 | 0261–0280 | ORF |
| 16910 | CsCsGsCsGsTsCsGsCsTsCsCsCsAsGsCsAsAsCsC | 2 | 0012–0031 | AUG |
| 16911 | GsCsTsGsAsGsCsTsCsTsTsAsGsCsAsAsGsCsAsGsT | 13 | scrambled control | (16374) |
| 16912 | GsTsGsCsCsCsTsGsCsCsCsAsCsCsGsAsCsCsAsC | 14 | scrambled control | (16371) |
| 17092 | AsGsTsGsCsGsCsAsTsGsTsCsAsAsCsGsAsCsGsT | 15 | scrambled control | (16374) |
| 17159 | ToGoAoGoGsCsTsAsCsCsTsGsGsAsCsAsCoAoGoToG | 5 | 0261–0280 | ORF |

[1] Emboldened residues, 2'-methoxyethoxy- residues (others are 2'-deoxy-) including "C" residues, 5-methyl-cytosines; "o", phosphodiester linkage; "s", phosphorothioate linkage.
[2] Co-ordinates from GenBank Accession No. Y00636, locus name "HSLFA3", SEQ ID NO:1.

Example 3

Assays for Antisense-Mediated Inhibition of LFA-3 Expression in HUVEC Cells

A. General Techniques

In order to evaluate the activity of potential human LFA-3-modulating oligonucleotides, human umbilical vein endothelial cells (HUVEC) from Clonetics Corporation (Walkersville, MD; alternatively, ATCC CRL-1730 from the American Type Culture Collection, Rockville, Md., can be used) were grown and treated with oligonucleotides or control solutions as detailed below. After harvesting, cellular extracts were prepared and examined for LFA-3 RNA and protein levels (e.g., Northern or flow cytometry assays, respectively). In all cases, "% expression" refers to the amount of LFA-3-specific signal in an oligonucleotide-treated cell relative to an untreated cell (or a cell treated with a control solution that lacks oligonucleotide), and "% inhibition" is calculated as: 100%−Expression=% Inhibition.

B. RNA Assays

The mRNA expression of each LFA-3 protein was determined by using a nucleic acid probe specifically hybridizable thereto in "Northern" assays. Nucleic acid probes specific for LFA-3 are described in the examples. The probes were radiolabelled by means well known in the art (see, e.g., *Short Protocols in Molecular Biology*, 2nd Ed., Ausubel et al., eds., John Wiley & Sons, New York, 1992, pages 3–11 to 2–3–44 and 4–17 to 4–18; Ruth, Chapter 6 in: *Methods in Molecular Biology, Vol. 26: Protocols for Oligonucleotide Conjugates*, Agrawal, ed., Humana Press Inc., Totowa, N.J., 1994, pages 167–185; and Chapter 10 In: *Molecular Cloning: A Laboratory Manual*, 2nd Ed., Sambrook et al., eds., pages 10.1–10.70). The blots were stripped and reprobed with a $^{32}$P-labeled glyceraldehyde 3-phosphate dehydrogenase (G3PDH) probe (Clontech Laboratories, Inc., Palo Alto, Calif.) in order to confirm equal loading of RNA and to allow the levels of LFA-3 transcripts to be normalized with regard to the G3PDH signals.

HUVEC (human) cells were grown in EGM (Clonetics, Walkersville, Md.) media containing 10% fetal bovine serum (FBS) in T-75 flasks until 80–90% confluent. At this time, the cells were washed 3x with 10 mL of Opti-MEM media (GIBCO-BRL). Then, 5 mL of Opti-MEM media containing 10 ug/mL LIPOFECTIN® (i.e., 1:1 (w/w) DOTMA/DOPE, where DOTMA=N-[1-(2,3-dioleyoxy)propyl]-N,N,N-trimethylammonium chloride and DOPE=dioleoyl phosphatidylethanolamine; GIBCO-BRL) and an appropriate amount of oligonucleotide were added to the cells (the time of addition of oligonucleotide is t=0h in the experiments described herein). As a control, cells were treated with LIPOFECTIN® without oligonucleotide under the same conditions and for the same times as the oligonucleotide-treated samples. After 4 hours at 37° C. (t=4h), the medium was replaced with fresh EGM media containing 10% FBS. The cells were typically allowed to recover for 2 hours. Total cellular RNA was then extracted in guanidinium, subjected to gel electrophoresis and transferred to a filter according to techniques known in the art (see, e.g., Chapter 7 In: *Molecular Cloning: A Laboratory Manual*, 2nd Ed., Sambrook et al., eds., pages 7.1–7.87, and *Short Protocols in Molecular Biology*, 2nd Ed., Ausubel et al., eds., John Wiley & Sons, New York, 1992, pages 2–24 to 2–30 and 4–14 to 4–29).

Following RNA transfer, filters were typically hybridized overnight to a probe specific for the particular LFA-3-encoding gene of interest in hybridization buffer (QUIKHYB™ hybridization solution, Stratagene, La Jolla, Calif.). This was followed by two washes in 2x SSC, 0.1% SDS at room temperature (~24° C.) for 15 minutes and one wash in 0.1x SSC, 0.2% SDS at 60° C. for 30 minutes. Hybridizing bands were visualized by exposure to X-OMAT AR film and quantitated using a PHOSPHORIMAGER® essentially according to the manufacturer's instructions (Molecular Dynamics, Sunnyvale, Calif.) Although quantitation via a PHOSPHORIMAGER® or a comparable instrument is a preferred means of measuring RNA levels, the results of these "Northern" assays could be determined by other means known in the art.

C. Protein Assays

HUVEC cells were grown in EGM (Clonetics, Walkersville, Md.) media with 10% FBS in 12 well plates flasks until 80–90% confluent. At this time, the cells were washed 3x with 10 mL of Opti-MEM media (GIBCO-BRL). Then, 500 μl of Opti-MEM media containing 10 μg/mL LIPOFECTIN® (i.e., 1:1 (w/w) DOTMA/DOPE, where DOTMA=N-[1-(2,3-dioleyoxy)propyl]-N,N,N-trimethylammonium chloride and DOPE=dioleoyl phosphatidylethanolamine; GIBCO-BRL) and an appropriate amount of oligonucleotide were added to the cells (the time of addition of oligonucleotide is t=0h in the experiments described herein). As a control, cells were treated with LIPOFECTIN® without oligonucleotide under the same conditions and for the same times as the oligonucleotide-treated samples. After 4 hours at 37° C. (t=4h), the medium was replaced with fresh EGM media containing 10% FBS. The cells were typically allowed to recover for 48 hours before protein extracts were prepared. Cells were washed and released by treatment with trypsin (GIBCO-BRL). Cells were stained with an appropriate fluorescently labeled primary antibody that specifically recognizes the LFA-3 protein under examination and the amount of each LFA-3 protein was determined by using fluorescence-activated cell sorting (FACS®) techniques (see, e.g., U.S. Pat. Nos. 4,727,020 to Recktenwald, 5,223,398 to Kortright et al., and 5,556,764 to Sizto et al.). The fluorescently labelled primary antibody specific for each LFA-3 protein is described in the appropriate Example. Alternatively, unlabelled primary antibodies to LFA-3 (some are described in the Examples) can be used and detected by the use of fluorescently-labelled secondary (i.e., specific for the primary antibody) antibodies.

In alternative methods for measuring LPA-3 levels, cell lysates and protein extracts are electrophoresed (SDS-PAGE), transferred to nitrocellulose filters and detected by means known in the art (see, e.g., Chapter 18 In: *Molecular Cloning: A Laboratory Manual*, 2nd Ed., Sambrook et al., eds., pages 18.34, 18.47–18.54 and 18.60–18.75)). Unlabelled primary antibodies to LFA-3 can be used and detected by means well known in the art including, for example, detection of the primary antibody by a secondary antibody that binds the primary antibody (see, e.g., *Short Protocols in Molecular Biology*, 2nd Ed., Ausubel et al., eds., John Wiley & Sons, New York, 1992, pages 10–33 to 10–35; and Chapter 18 In: *Molecular Cloning: A Laboratory Manual*, 2nd Ed., Sambrook et al., eds., pages 18.1–18.75 and 18.86–18.88) and quantitated using other antibody-based assays known in the art. Such antibody-based assays include, but are not limited to, ELISA assays, Western assays, and the like (see, for example, U.S. Pat. Nos. 4,879,219 to Wands et al. and 4,837,167 to Schoemaker et al., and *Short Protocols in Molecular Biology*, 2nd Ed., Ausubel et al., eds., John Wiley & Sons, New York, 1992, pages 11–5 Lo 11–17). LFA-3 activity can be measured in appropriate cell adhesion assays and model systems known in the art (Dustin et al., *Annu. Rev. Immunol.*, 1991, 9, 27).

Example 4

Antisense-Mediated Inhibition of Human LFA-3 Expression by Oligonucleotides

A. Activities of LFA-3 Oligonucleotides

In an initial screen for active compounds capable of modulating LFA-3 expression, HUVEC cells were treated with 10 nM of a series of LFA-3-specific "gapmer" oligonucleotides (ISIS Nos. 16371–16381, 16909–16912, 17092 and 17159; SEQ ID NOS: 2–15) and LFA-3 protein levels were determined by FACS® using a monoclonal antibody to LFA-3 (CD58) conjugated to phycoerythrin (PE) from Pharmingen (San Diego, Calif.). Isotypic (mouse IgG-2a kappa) control antibody (also from Pharmingen) typically gave signals of ≦5% of the basal signal. PE- and FITC-labeled antibodies to LFA-3 are available from, for example, Immunotech (Westbrook, Me.), Serotec (Oxford, England), Biodesign International (Kennebunk, Me.), Research Diagnostics, Inc. (RDI, Flanders, N.J.). Other primary antibodies to LFA-3 suitable for FACS® analysis in combination with a labelled secondary antibody are available from the above vendors and, e.g., Endogen (formerly T Cell Diagnostics, Woburn, Mass.) and Upstate Biotechnology (Lake Placid, N.Y.).

The data from the screening (Table 2) indicate the following results. Oligonucleotides showing activity in this assay, as reflected by levels of inhibition≧about 30% of LFA-3 protein levels, where "about" indicates ±5%, include ISIS Nos. 16371, 16373, 16374, 16376, 16377, 16378, 16909, 16910 and 17159 (SEQ ID NOS: 2, 4, 5, 7, 8, 9, 5, 2, and 5, respectively). These oligonucleotides are thus preferred embodiments of the invention for modulating LFA-3 expression. Oligonucleotides showing levels of inhibition≧about 50% of LFA-3 in this assay, where "about" indicates ±5%, include ISIS Nos. 16371, 16374, 16910 and 17159 (SEQ ID NOS: 2, 5, 2 and 5, respectively). These oligonucleotides are thus most preferred embodiments of the invention for modulating LFA-3 expression.

TABLE 2

Activities of Antisense Oligonucleotides Targeted to Human LFA-3[1]

| ISIS No: | SEQ ID NO: | GENE TARGET REGION | % PROTEIN EXPRESSION | % PROTEIN INHIBITION |
|---|---|---|---|---|
| basal | — | LIPOFECTIN ® only | 100% | 0% |
| 16371 | 2 | AUG | 51.2% | 48.8% |
| 16372 | 3 | ORF | 88.5% | 11.5% |
| 16373 | 4 | ORF | 66.8% | 33.2% |
| 16374 | 5 | ORF | 46.7% | 53.3% |
| 16375 | 6 | ORF | 84.9% | 15.1% |
| 16376 | 7 | stop | 63.3% | 36.7% |
| 16377 | 8 | 3'-UTR | 67.8% | 32.2% |
| 16378 | 9 | 3'-UTR | 71.4% | 28.6% |

TABLE 2-continued

Activities of Antisense Oligonucleotides Targeted to Human LFA-3[1]

| ISIS No: | SEQ ID NO: | GENE TARGET REGION | % PROTEIN EXPRESSION | % PROTEIN INHIBITION |
|---|---|---|---|---|
| 16379 | 10 | 3'-UTR | 84.7% | 15.3% |
| 16380 | 11 | 3'-UTR | 81.5% | 18.5% |
| 16381 | 12 | 3'-UTR | 77.9% | 22.1% |
| 16909 | 5 | ORF | 66.0% | 34.0% |
| 16910 | 2 | AUG | 52.8% | 47.2% |
| 16911 | 13 | (control - 16374) | 86.4% | 13.6% |
| 16912 | 14 | (control - 16371) | 103.0% | — |
| 17092 | 15 | (control - 16374) | 105.0% | — |
| 17159 | 5 | ORF | 41.0% | 59.0% |

[1]Oligonucleotide concentration = 10 nM, t = 4 h.

B. Dose Response and Sequence Specificity

The dose response of LFA-3 protein expression in HUVEC cells following 4 hours of treatment with various concentrations of ISIS Nos. 16371, 16374, 16375 and 13315 is shown in Table 3. ISIS 13315 (SEQ ID NO:16) is a antisense oligonucleotide targeting mouse ICAM-1 and was used as a non-related sequence control. Levels of LFA-3 protein were determined by FACS® as above. Under these conditions, active antisense oligonucleotides ISIS 16371 and ISIS 16374 gave about 45% and 70%, respectively, inhibition of LFA-3 protein levels, where "about" indicates ±5%, when applied at a concentration of 10 nM. In contrast, an inactive antisense oligonucleotide ISIS 16375 gave minimal inhibition, i.e., ≦about 15% inhibition. For ISIS 16371, the degree of inhibition increased to about 65% at 30 nM. For ISIS 16374, the degree of inhibition increased to about 80% at 30 nM.

The specificity of modulation of LFA-3 by the antisense oligonucleotides was confirmed using ISIS No. 13315 as a control. The results demonstrate that treatment of cells with the control oligonucleotide had little effect on LFA-3 protein expression. This result agrees with the results presented in Table 2 for the scrambled control oligonucleotides ISIS Nos. 16911, 16912, 17092. These scrambled control oligonucleotides also gave minimal inhibition of LFA-3, i.e., <about 10%, where "about" indicates ±5%. These results demonstrate that the LFA-3-modulating activity of the active antisense compounds is sequence-specific.

TABLE 3

Dose Response of HUVEC Cells to, and Sequence Specificity of, LFA-3 Antisense Oligonucleotides (ASOs)[1]

| ISIS # | SEQ ID NO: | ASO Gene Target | Dose | % Protein Expression | % Protein Inhibition |
|---|---|---|---|---|---|
| basal | — | LIPOFECTIN ® only | 0 nM | 100.0% | 0.0% |
| 16371 | 2 | AUG | 1 nM | 101.7% | — |
| 16371 | 2 | " | 3 nM | 83.9% | 16.1% |
| 16371 | 2 | " | 10 nM | 56.8% | 43.2% |
| 16371 | 2 | " | 30 nM | 34.9% | 65.1% |
| 16374 | 5 | ORF | 1 nM | 75.6% | 24.4% |
| 16374 | 5 | " | 3 nM | 58.4% | 41.6% |
| 16374 | 5 | " | 10 nM | 29.1% | 70.9% |
| 16374 | 5 | " | 30 nM | 20.0% | 80.0% |
| 16375 | 6 | ORF | 1 nM | 94.3% | 5.7% |
| 16375 | 6 | " | 3 nM | 98.0% | 2.0% |
| 16375 | 6 | " | 10 nM | 91.9% | 8.1% |
| 16375 | 6 | " | 30 nM | 84.2% | 15.8% |

TABLE 3-continued

Dose Response of HUVEC Cells to, and Sequence Specificity of, LFA-3 Antisense Oligonucleotides (ASOs)[1]

| ISIS # | SEQ ID NO: | ASO Gene Target | Dose | % Protein Expression | % Protein Inhibition |
|---|---|---|---|---|---|
| 13315 | 16 | mouse ICAM-1 | 1 nM | 84.1% | 15.9% |
| 13315 | 16 | mouse ICAM-1 | 3 nM | 95.4% | 4.6% |
| 13315 | 16 | mouse ICAM-1 | 10 nM | 107.4% | — |
| 13315 | 16 | mouse ICAM-1 | 30 nM | 122.6% | — |

[1]t = 4 h.

C. Confirmation of Antisense Mechanism

In order to confirm that the oligonucleotides identified as active work by an antisense mechanism, the following experiments were performed to assay LFA-3 mRNA levels. To prepare an LFA-3-specific nucleic acid probe, radiolabelled LFA-3-specific PCR product was prepared using RNA from HUVEC cells and a pair of phosphodiester oligonucleotides, —5'-CAGCGTGGTCTGCCTGCTGC (SEQ ID NO: 17); and —5'-GTTATGCTGTTGTCTTCATC (SEQ ID NO: 18), as primers in PCR reactions using a PRIME-A-GENE® labeling kit (Promega, Madison, Wis.). The resultant $^{32}$P-cytosine-radiolablled 743-bp product hybridizes to the open reading frame of human LFA-3 (SEQ ID NO: 1). Alternatively, however, other PCR probes can be prepared, or one or more of the oligonucleotides of Table 1 can be detectably labeled and used as LFA-3-specific probes using methods known in the art.

Northern assays were performed as described in Example 3 using the above probe. HUVEC cells were treated with 5 nM of antisense oligonucleotide and RNA was harvested at t=h. The experiment was performed three and the results were quantitated using a PHOSPHORIMAGER® and normalized to mRNA encoding glyceraldehyde 3-phosphate dehydrogenase (G3PDH). The results (Table 4) demonstrate that ISIS 16374 reduces LFA-3 mRNA levels by almost 85%, whereas a control (scrambled) oligonucleotide had little effect on LFA-3 mRNA levels. Thus, the compounds of the invention exert their effect via a bona fide antisense mechanism.

TABLE 4

Antisense-Mediated Reduction of LFA-3 mRNA Levels

| ISIS No: | SEQ ID NO: | Relative Level of LFA-3 mRNA | Standard Deviation |
|---|---|---|---|
| basal | — | 1.01 | 0.13 |
| 16374 | 5 | 0.17 | 0.02 |
| 17092 | 15 | 0.95 | 0.18 |

D. Preferred Regions for Antisense Modulation of Nucleic Acids Encoding Human LFA-3

The antisense compounds of the invention may be designed to be specifically hybridizable (targeted) to any portion of a nucleic acid encoding LFA-3. However, the above results indicate that several regions, and sequences within such regions, of nucleic acids encoding human LFA-3 are particularly preferred for antisense modulation of, and are thus preferred target regions for antisense compounds designed to modulate, human LFA-3.

1. The AUG (start) codon region of human LFA-3 is the target region for ISIS 16371 and 16910 (SEQ TD NO: 2), a preferred embodiment of the invention.

2. The ORF (open reading frame) region of human LFA-3 is the target region for ISIS 16373, 16374, 16909 and 17159 (SEQ ID NOS: 4 and 5), all of which are preferred embodiments of the invention.

3. The stop codon region of human LFA-3 is the target region for ISIS 16376 and 16377 (SEQ ID NOS: 7 and 8), all of which are preferred embodiments of the invention. As is shown in FIG. 1, these antisense compounds encompass base pairs 760 to 800 of the human LFA-3 sequence (SEQ ID NO: 1), and this region (SEQ ID NO: 19) is thus a preferred target region for antisense compounds designed to modulate human LFA-3.

4. The 3'-UTR (untranslated region) of human LFA-3 is the target region for ISIS 16378 (SEQ ID NO: 9), a preferred embodiment of the invention.

E. Targeting of Different Isoforms of LFA-3

In addition to the transmembrane form of LFA-3 encoded by SEQ ID NO: 1 (Wallner et al., *J. Exp. Med.*, 1987, 166, 923), two isoforms of LFA-3 are known. Certain of the antisense compounds of the invention may be directed to particular isoforms in order to achieve specific effects.

"PI-linked LFA-3" (a.k.a. PI-linked CD58) is an isoform of LFA-3 that is anchored to the cell membrane via a covalent linkage to phosphatidylinositol (PI). Although PI-linked LFA-3 is displayed on the cell surface and thus may contribute to cell:cell association, it does not cross the cell membrane and thus probably does not effect signal transduction. The nucleotide sequence of a cDNA encoding PI-linked LFA-3 (Seed, Nature, 1987, 329, 840) diverges from that encoding the transmembrane isoform (SEQ ID NO: 1) at positions 719–1040. Accordingly, antisense compounds targeted to this region, including but not limited to ISIS 16376, 16377 arid 16378 (SEQ ID NOS: 7, 8 and 9), are expected to reduce or inhibit the expression of the transmembrane form of LFA-3 without significant impact on the expression of PI-linked LFA-3.

"Soluble LFA-3" (a.k.a. sLFA-3 or sCD58) has been identified in human serum and urine and in culture supernatants of several human cell lines (Hoffman et al., *Eur. J. Immunol.*, 1993, 23, 3003). The in vivo mechanism by which sLFA-3 is produced has not been characterized but, based on similar biological systems, could arise from either (1) alternate splicing of RNA encoding LFA-3 to produce an mRNA that encodes an isoform that lacks the transmembrane domain or (2) proteolytic cleavage of membrane-bound LFA-3 protein. While not wishing to bound by any particular theory, if sLFA-3 is produced by alternate splicing, antisense compounds targeted to the portion of RNA encoding the transmembrane domain of LFA-3 are expected to reduce or inhibit the expression of the transmembrane form of LFA-3 without significant impact on the expression of sLFA-3. The transmembrane domain is encoded by bases 655–1040 of SEQ ID NO: 1 (Wallner et al., *J. Exp. Med.*, 1987, 166, 923) and antisense compounds specifically targeted to this region include, but are not limited to, TSIS 16376, 16377 and 16378 (SEQ ID NOS: 7, 8 and 9). Such antisense compounds are expected to reduce or inhibit the expression of the transmembrane form of LFA-3 produced by alternate RNA splicing without significant impact on the expression of soluble LFA-3.

Example 5

Antisense-Mediated Inhibition of T Cell Stimulation

Studies have indicated that human endothelial cells (ECs) effectively costimulate interleukin 2 (IL-2), interleukin 4 (IL-4) and interferon-gamma (IFN-γ) production from r cells activated by phytohemagglutinin (PHA). Blocking experiments with monoclonal antibodies to LFA-3 suggest that LFA-3:CD2-mediated signaling contributes about 50% of the costimulation by ECs (Hughes et al., *J. Exp. Med.*, 1990, 171, 1453). In order to assess the ability of the antisense compounds of the invention to modulate the ability of cells to activate T cells, as measured by cytokine production and T cell proliferation, the following experiments were performed.

A. PHA Costimulaton Assay

Serially cultured HUVEC cells were treated with 25 nM of ISIS 16374 (active LFA-3 oligonucleotide) or 17092 (scrambled control for 16374) in six-well tissue FALCON® culture plates (Becton-Dickinson and Co., Franklin Lakes, N.J.) using LIPOFECTIN® as described in the previous Examples. A sample of the treated cells were analyzed 70 hours later for surface expression of LFA-3 via FACS® analysis, as in the previous Examples, using FITC-conjugated anti-CD5S (Immunotech, Westbrook, Me.). Surface expression of LFA-3 on ISIS 16374-treated HUVEC cells was reduced to 20–25. of that expressed on the surface of cells treated with the scrambled control oligonucleotide ISIS 17092. The remaining cells were replated in tissue culture round-bottom 96-well plates for the following costimulation assays.

CD4$^+$ T cells were isolated from peripheral blood monocytes (PBMC) from adult volunteer donors by negative selection, and the resulting cells were about 90% CD4$^+$. Approximately 2,000 purified CD4$^+$ T cells were added to each well in RPMI 1640 media (Life Technologies, Inc., Gaithersburg, Md.) containing 10% fetal calf serum (FCS), 2.5 mM glutamine, 100 U/ml penicillin and 100 ug/mL streptomycin (all from Life Technologies) in a final volume of 200 μL. The T cell mitogen phytohemagglutinin (PHA-L from Sigma Chemical Co., St. Louis, Mo.) was also added to the media at 3 ug/mL.

For purposes of comparison, blocking antibody IF6 (anti-CD58, isotype IgG1, gift from Biogen, Cambridge, Mass.) was added at 50 ug/mL; as a control, K16/16 (non-binding TgC1, ascites fluid) was added at a 1:1000 dilution. Other anti-CD58 blocking antibodies such as, for example, catalog No. 8-4758N from Perceptive Diagnostics, Cambridge, Mass., or deposit No. 91060558 of the European Collection of Animal Cell Cultures, Salisbury, U.K., may be used. Media was collected 24 hours later and assayed for various T cell-produced cytokines using human IL-2, IFN-γ and IL-4 ELISA kits (Coulter Corp., Miami, Fla.)

Figure 2B:
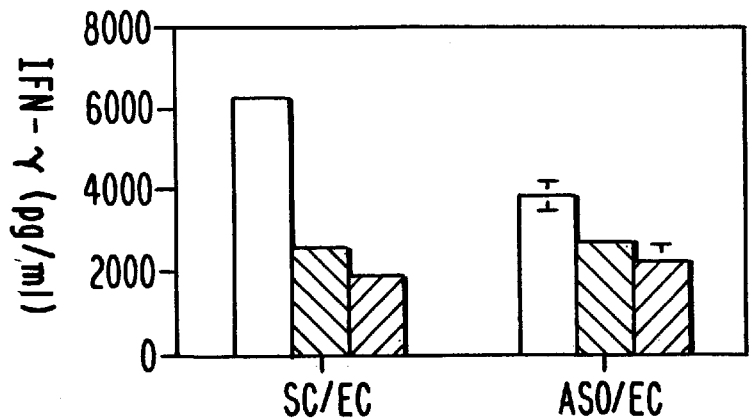
Figure 2C:
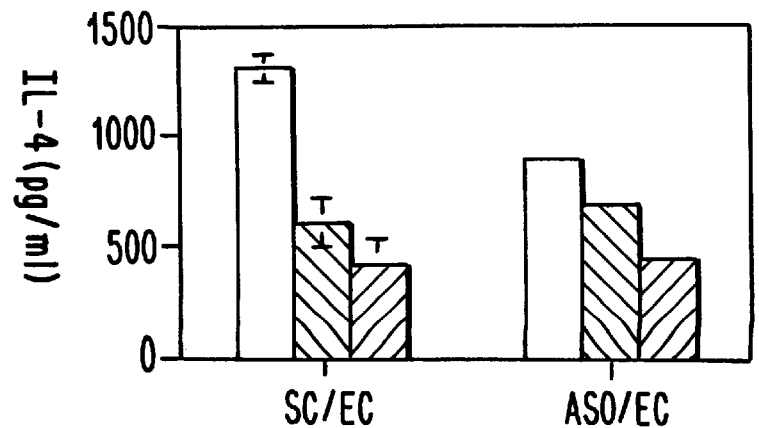

The results are shown in FIG. 2, wherein each data point represents the mean of two wells. The scrambled control (SC) oligonucleotide ISIS 17092 had no effect on the production of the three cytokines ("SC/EC," open boxes) and did not inhibit the ability of monoclonal antibodies to LFA-3 or CD2 to reduce cytokine production ("SC/EC," hatched and filled boxes, respectively). In contrast, the active antisense oligonucleotide (ASO) ISIS 16374 was nearly as effective as antibodies to LFA-3 or CD2 in inhibiting cytokine production ("ASO/EC," open boxes). No further reduction in cytokine production was seen when ISIS 16374 was combined with the antibodies ("ASO/EC," hatched and filled boxes).

B. Alloreactions

Previous studies have shown that IFN-γ-treated cultured ECs are able to activate allogeneic CD4$^+$ cells to secrete cytokines and to proliferate, and that monoclonal antibodies to LFA-3 inhibit this alloreaction (Savage et al., *Transplantation*, 1993, 56, 128). Alloreactions were set in a similar manner as the PHA costimulation assays, except that co-cultures were established in flat bottom plates and no PHA was added. ECs were plated at low confluency 4 days before [d(−4)] addition of CD4$^+$ T cells and immediately treated with 500 U/mL human IFN-γ to induce class II MHC expression. The ECs were treated with oligonucleotides on d(−3), replated on d(−1) treated with 10 ug/mL of mitomycin C (Sigma) for 1 hour and washed before the addition of 3×10$^5$ purified CD4$^+$ T cells on do.

The medium from these co-cultures was collected on d1, d2 or d3 for cytokine assays using ELISA kits. in experiments where IL-2 was measured, anti-TAC was added at 10 mg/mL in order to prevent cellular uptake of IL-2 from the media. Anti-TAC is a monoclonal antibody that binds to the alpha chain of the IL-2 receptor and blocks its interaction with IL-2 (gift from Tom Waldmann and commercially available from BioSource International, Camarillo, Calif.). In addition, during the last 18 to 24 hours of co-cultures on d4, d5, d6 or d7, 1 μCi of [$^3$H] thymidine as added to each well, and T cell proliferation was assessed by [3H] incorporation. The plates were harvested with a 96-well harvester (Tomtec Co. Ltd., Tokyo, Japan) and counted on a Microbeta scintillations counter (EC&C Wallac, Turku, Finland). The results are shown in FIGS. 3 and 4, wherein each data point represents the mean of three replicate wells.

Figure 3A:
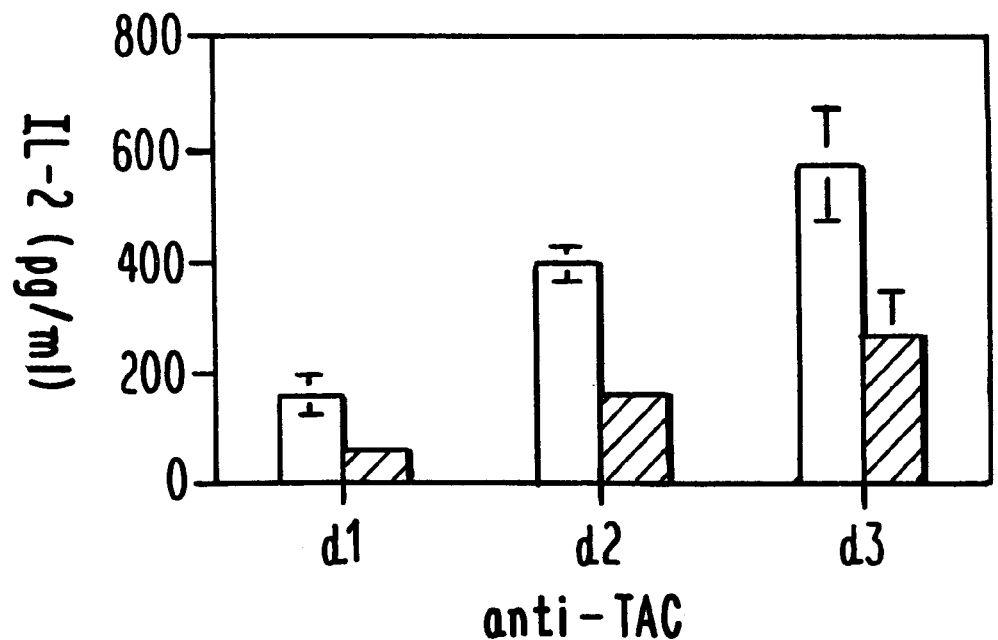
FIG. 3 shows that pretreatment of human endothelial cells with antisense oligonucleotides inhibits cytokine production by allogeneic $CD4^+$ T cells. As indicated, a monoclonal antibody to alpha chain of the IL-2 receptor (i.e., "anti-TAC") was added in the experiments of the upper panel in order to prevent IL-2 utilization. Symbols: open boxes, scrambled control oligonucleotide (ISIS 17092); filled boxes, active antisense oligonucleotide (ISIS 16374).
Figure 3B:
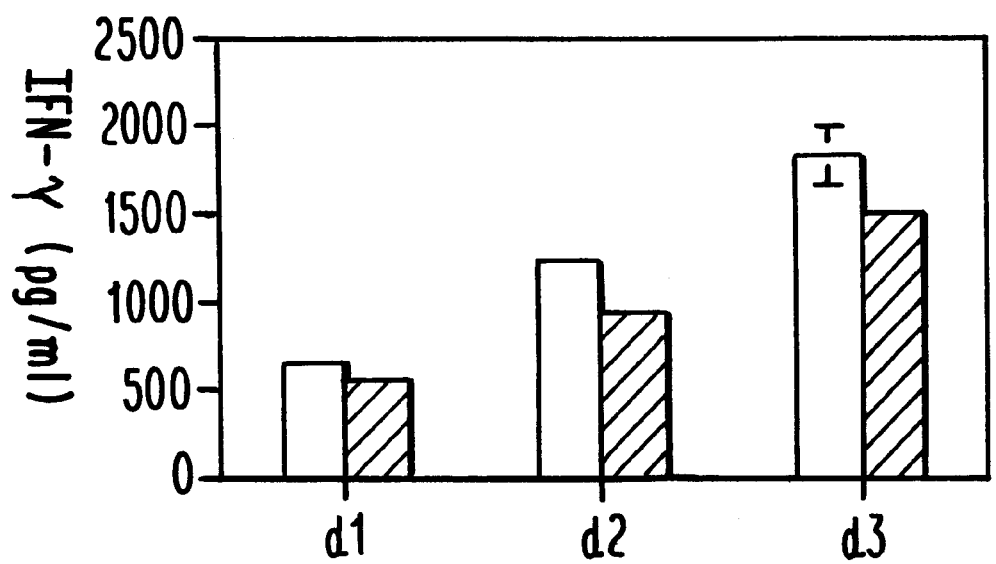

As shown in FIG. 3, pretreatment of ECs with the active antisense oligonucleotide ISIS 16374 (closed boxes) inhibited production of IL-2 and IFN-γ relative to the scrambled control oligonucleotide 17092 (open boxes). ISIS 16374 on IL-2 maintained a level of about 50% inhibition for at least 3 days, although its effect on IFN-γ was less striking.

Figure 4A:
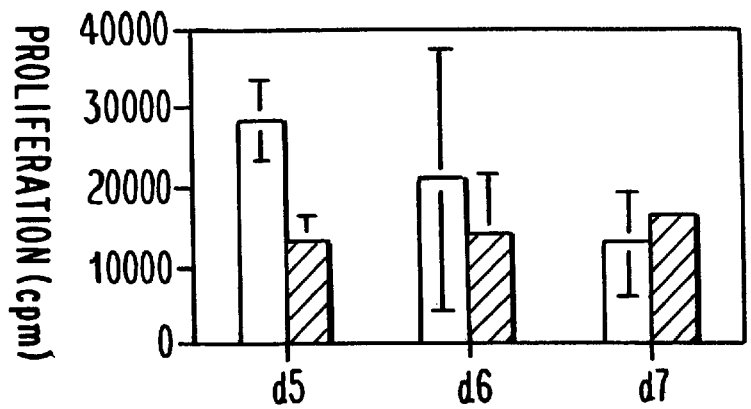
FIG. 4 shows that pretreatment of human endothelial cells with antisense oligonucleotides inhibits the proliferation of allogeneic $CD4^+$ cells. Symbols: open boxes, scrambled control oligonucleotide (ISIS 17092); filled boxes, active antisense oligonucleotide (ISIS 16374).
Figure 4B:
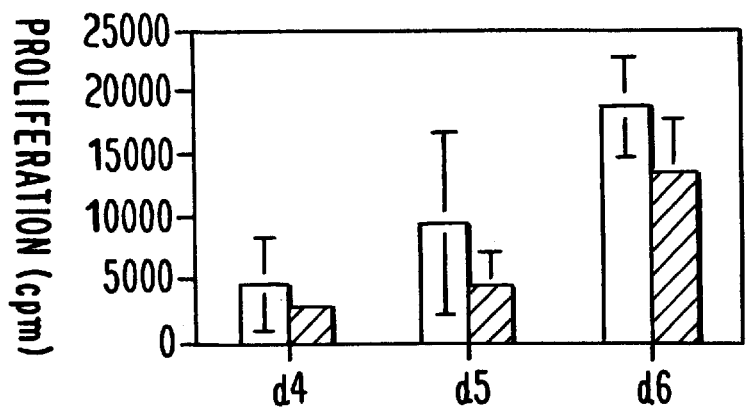
Figure 4C:
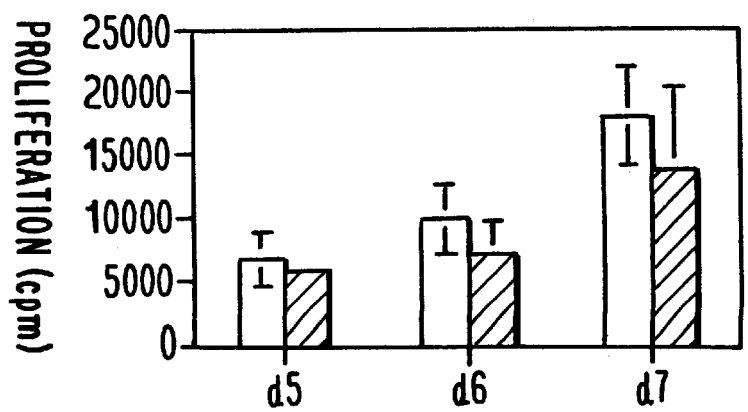

Results from three independent proliferation assays are shown in FIG. 4. The alloresponse is somewhat variable; the degree of inhibition of peak proliferative response ranged from about 20% to about 50%. However, in all cases, the peak proliferative response is inhibited by pretreatment of ECs with ISIS 16374.

These results demonstrate that the antisense compounds of the invention specifically inhibit LFA-3 expression on human endothelial cells and that such treatment reduces the capacity of such cells to activate T cells to at least the same degree as monoclonal antibodies to LFA-3 or CD2.

Example 6

Therapeutic Methods

The antisense compounds of the invention result in immunosuppressive and anti-inflammatory effects in vivo and may be used by those skilled in the art to provide prophylactic, palliative and therapeutic benefit to an animal, including a human, in need of such effects. The antisense compounds of the invention are also evaluated for their ability to inhibit the metastasis of cancer cells and are used to provide prophylactic, palliative or therapeutic relief from hyperproliferative disorders. Therapeutic methods using the antisense compounds of the invention include, but are not limited to, the following examples.

A. Modulation of Undesirable Immunoresponsive Events

The present invention provides a method of modulating immunoresponsive events that are mediated or influenced, either directly or indirectly, by LFA-3 in an animal. Such immunoresponsive events can lead to undesirable effects such as, e.g., inflammation. The method of modulating immunoresponsive events mediated or influenced by LFA-3 comprises administering one or more of the antisense compounds of the invention (or a combination thereof with one or more anti-inflammatory or immunosuppressive non-antisense-based agents or NABAs; see below), in a pharmaceutical preparation if required, to the animal. Some specific therapeutic modalities for the antisense compounds of the invention follow as examples but are not intended to limit the scope of the invention.

1. Events Mediated by LFA-3 and CD2

The present invention provides compositions and methods for inhibiting LFA-3 expression. Because the binding of LFA-3 to CD2 is required to trigger a series of subsequent molecular and/or cellular events, inhibition of LFA-3 expression is expected to result in the reduction or inhibition of such events. A variety of in vitro and in viva methods are available to assay the ability of the antisense compounds of the invention to inhibit LFA-3:CD2 interactions (see, for example, Dustin et al., *J. Cell Biol.*, 1996, 132, 465; Ding et al., *J. Immunol.*, 1996, 157, 1863).

2. T Cell Activation

The present invention provides a method of modulating LFA-3-mediated T cell activation in an animal comprising administering one or more of the antisense compounds of the invention, or a combination thereof with one or more anti-inflammatory or immunosuppressive agents, in a pharmaceutical preparation if required, to the animal. Soluble forms of LFA-3, which compete with cell surface LFA-3 for membrane-bound CD2, interfere with T cell activation (Yamashita et al., *Immunol.*, 1997, 92, 39). Undesired LFA 3-mediated or -associated T cell activation is thought to be an important component in many injurious immune responses, including inflammation, asthma, chronic liver disease including alcoholic cirrhosis, and the like (Mengelers et al., *Am. J. Respir. Crit. Care Med.*, 1994, 149, 345; Hoffman et al., *J. Hepatol.*, 1996, 25, 465; Santos-Perez et al., *Immunol. Lett.*, 1996, 50, 179). Administration of the antisense compounds of the invention, as part of an appropriate pharmaceutical composition if required, to an animal is expected to inhibit T cell activation and subsequent undesired immunoresponsive events such as, for example, inflammation and inflammatory damage. Such treatment may be in combination with one or more anti-inflammatory and/or immunosuppressive NABAs and, additionally or alternatively, with one or more additional antisense compounds targeted to, for example, a CAM protein, a B7 protein, or a protein kinase C (see below). Such administration can be systemic or directly to the site(s) of inflammation and/or inflammatory damage. The antisense compounds of the invention are evaluated for their ability to modulate T cell activation and subsequent undesired inflammation and/or inflammatory damage using, for example, the assays described in Example 5 and/or other appropriate in vitro or in vivo models.

3. Allograft Rejection and GVHD

The present invention also provides a method of avoiding allograft rejection including treating or preventing graft versus host disease (GVHD) in an animal comprising administering one or more of the antisense compounds of the invention, or a combination thereof with one or more anti-inflammatory or immunosuppressive agents, in a pharmaceutical preparation if required, to the animal. Inhibition of LFA-3:CD2 interactions by a soluble LFA-3-IgG1 fusion protein has been shown to prolong primate cardiac allograft survival and to protect xenografted skin tissue in immunodeficient mouse/human chimeras (Kaplon et al., *Transplantation*, 1996, 61, 356; Sultan et al., *Nature Biotech.*, 1997, 15, 759). Accordingly, administration of one or more of the LFA-3-modulating antisense compounds of the invention (in combination with other agents and as part of an appropriate pharmaceutical composition if required) to an animal is expected to modulate xenograft or allograft rejection and GVHD.

Administration of the antisense compounds of the invention in this method may be systemic or directly to the area(s) of the transplanted tissue(s) or organ(s), or administered ex vivo to tissue(s) or organ(s) prior to their transplantation. Such treatment may be in combination with one or more anti-inflammatory/immunosuppressive NABAs and, additionally or alternatively, with one or more additional antisense compounds targeted to a CAM protein, a B7 protein, or a protein kinase C (see below). The antisense compounds of the invention are evaluated for their ability to modulate allograft rejection using one or more assays known in the art and/or one or more appropriate animal models (see, e.g., Stepkowski et al., *J. Immunol.*, 1994, 153, 5336, and Example 21 in U.S. Pat. No. 5,514,788 to Bennett et al., hereby incorporated by reference).

5. Arthritis

The present invention also provides a method of treating various forms of arthritis in an animal comprising administering one or more of the antisense compounds of the invention, or a combination thereof with one or more anti-inflammatory or immunosuppressive agents, in a pharmaceutical preparation if required, to the animal. Such administration can be systemic or directly to involved tissues such as, e.g., synovial fluid. A soluble form of LFA-3 (CD58) has been identified in the synovial fluid of patients with rheumatoid arthritis (RA) and is found at decreased levels in RA patients relative to levels found in humans not having RA (Hoffman et al., *Clin. Exp. Immunol.*, 1996, 104, 460; Hoffman et al., *Clin. Exp. Rheumatol.*, 1996, 14, 23). Accordingly, administration of one or more of the LFA-3-modulating antisense compounds of the invention (in combination with other agents and as part of an appropriate pharmaceutical composition if required) to an animal is expected to modulate RA.

Administration of the antisense compounds of the invention to treat RA may be in combination with one or more additional antisense compounds or anti-inflammatory/immunosuppressive NABAs (see below). The antisense compounds of the invention are evaluated for their ability to modulate arthritis and inflammatory damage resulting therefrom using one or more assays known in the art and/or one or more appropriate animal models (see, e.g., published PCT application No. WO 95/32285 to Benoist et al.).

6. Inflammatory Disorders of the Bowel

The present invention also provides a method of treating various inflammatory disorders of the bowel in an animal comprising administering one or more of the antisense compounds of the invention, or a combination thereof with one or more anti-inflammatory or immunosuppressive agents, in a pharmaceutical preparation if required, to the animal. Such disorders include, for example, Crohn's disease (CD) and other forms of regional enteritis; and various forms of colitis including ulcerative colitis (UC) and granulomatous, ischemic and radiation colitis (see *The Merck Manual of Diagnosis and Therapy*, 15th Ed., pp.

797–806, Berkow et al., eds., Rahay, N.J., 1987). An in vitro model of Crohn's disease, in which cellular aggregates similar to tissue granulomas found in the disease are formed, has been described. Blocking antibodies to LFA-3 inhibit in vitro aggregate formation in this model (Mishra et al., Gastroenterol., 1993, 104, 772). Moreover, as is the case with RA, levels of soluble LFA-3 are reduced in patients with inflammatory bowel disease (Hoffman et al., Z. Gastroenterol., 1996, 34, 522). These findings indicate that administration of one or more of the LFA-3-modulating antisense compounds of the invention (in combination with other agents and as part of an appropriate pharmaceutical composition if required) to an animal might be expected to modulate Crohn's disease and other inflammatory disorders of the bowel.

Administration of the antisense compounds of the invention to treat such disorders may be in combination with one or more additional antisense compounds or anti-inflammatory and/or immunosuppressive NABAs (see below). The antisense compounds of the invention are evaluated for their ability to modulate a inflammatory disorder of the bowel using one or more assays known in the art and/or one or more appropriate animal models (see, e.g., Okayasu et al., Gastroenterol., 1990, 98, 694; Mishra et al., Gastroenterol., 1993, 104, 772; and Example 20 in U.S. Pat. No. 5,514,788 to Bennett et al., hereby incorporated by reference).

7. Autoimmune Diseases and Disorders

The present invention also provides a method of treating various autoimmune diseases and disorders including but not limited to autoimmune thyroid disorders; autoimmune forms of arthritis; multiple sclerosis (MS); some forms of juvenile diabetes mellitus; myasthenia gravis; pemphigus vulgaris; and systemic lupus erythematosus (SLE or lupus) (for a review of autoimmune disorders, see Steinman, Sci. Amer., 1993, 269, 107). A preferred embodiment of the invention involves the treatment or prevention of autoimmune thyroid disorders, such as, e.g., Graves' Disease (thyrotoxicosis), Hashimoto's disease and De Quervain thyroiditis, as LFA-3 has been observed to be expressed in such conditions (Zheng et al., J. Autoimmun., 1990, 3, 727). Administration of the antisense compounds of the invention, as part of an appropriate pharmaceutical composition if required, to an animal is expected to prevent or inhibit the development of the autoimmune disease and subsequent undesired events. Such treatment may be in combination with one or more anti-inflammatory/immunosuppressive NABAs and, additionally or alternatively, with one or more additional antisense compounds targeted to, for example, a CAM protein, a B7 protein, or a protein kinase C (see below). Such administration can be systemic or directly to a specific tissue, depending on the nature of the disorder. For example, systemic administration might be more appropriate for SLE, whereas direct administration to the thyroid gland or adjacent tissues might be more efficacious in the case of Graves' Disease. The antisense compounds of the invention are evaluated for their ability to prevent or inhibit autoimmune diseases using appropriate assays and animal models known to those skilled in the art (see, for example, Burkhardt et al., Rheumatol. Int., 1997, 17, 91).

B. Treatment of Hyperproliferative Disorders

Patients having benign tumors, and primary malignant tumors that have been detected early in the course of their development, may often be successfully treated by the surgical removal of the benign or primary tumor. If unchecked, however, cells from malignant tumors are spread throughout a patient's body through the processes of invasion and metastasis. Invasion refers to the ability of cancer cells to detach from a primary site of attachment and penetrate, e.g., an underlying basement membrane. Metastasis indicates a sequence of events wherein (1) a cancer cell detaches from its extracellular matrices, (2) the detached cancer cell migrates to another portion of the patient's body, often via the circulatory system, and (3) attaches to a distal and inappropriate extracellular matrix, thereby creating a focus from which a secondary tumor can arise. Normal cells do not possess the ability to invade or metastasize and/or undergo apoptosis (programmed cell death) if such events occur (Ruoslahti, Sci. Amer., 1996, 275, 72).

Disseminating precancerous or cancerous cells often display ectopic expression of adhesion molecules which may facilitate step (3) of the metastatic process as described above. Examples of such adhesion molecules include ICAM-1 and other CAMs (for a review, see Tang et al., Invasion Metastasis, 1994, 14, 109). LFA-3 is also associated with some hyperproliferative diseases, such as various myelomas (Cook et al., Acta Haematol., 1997, 97, 81; Tatsumi et al., Jpn. J. Cancer Res., 1996, 87, 837), bladder tumors (Nouri et al., 1996, Urol. Tnt. 56, 6) and adult T-cell leukemia (Imai et al., Tnt. J. Cancer, 1993, 55, 811). Thus, modulation of one or more CAMs using the antisense compounds of the invention may result in a decreased ability of disseminating cancer cells to attach to a distal and/or inappropriate matrix, thereby modulating metastasis of the primary tumor.

The present invention thus also provides a method of modulating or preventing metastasis in an animal comprising administering one or more of the antisense compounds of the invention, in a pharmaceutical preparation if required, to the animal. Such treatment may be in combination with one or more additional antisense compounds or anticancer chemotherapeutic NABAs (see below). The antisense compounds of the invention are evaluated for their ability to modulate metastasis using one or more assays known in the art and/or one or more appropriate animal models (see, e.g., Examples 16–18 in U.S. Pat. No. 5,514,788 to Bennett et al., hereby incorporated by reference).

C. Treatment of Diseases Caused by Pathogens

Several studies have implicated LFA-3 expression and or function with enhanced pathogenicity of human viruses. For example, LFA-3 is upregulated in fibroblasts infected with cytomegalovirus (Grundy et al., Immunol., 1993, 78, 405), and this effect is not blocked by treatment with the antiviral NABAs ganciclovir and foscarnet (Craigen et al., Transplantation, 1996, 62, 1102). Accordingly, despite conventional antiviral treatment in a transplant recipient, CMV-infected donor cells may overexpress LFA-3 and thus be proinflammatory in nature, a characteristic which could contribute to immunopathology or accentuate GVHD or allograft rejection. Treatment of the recipient animal in vivo, and/or of donor cells or tissues ex vivo, with the antisense compounds of the invention, in combination with antiviral NABAs if need be, is expected to prevent or limit such undesired effects.

In the case of human immunodeficiency virus (HIV), studies have demonstrated that engagement of LFA-3 (CD58) by soluble antibodies thereto enhances HIV replication (Shattock et al., J. Infect. Dis., 1996, 174, 54). This effect may be due to a signal transduction mechanism, as that antibodies to the LFA-3 ligand, CD2, activate transcription from the long terminal repeat of HIV in T cells (Bressler et al., J. Immunol., 1991, 147, 2290). Accordingly, treatment of individuals with the antisense compounds of the invention is expected to limit the growth and spread of HIV.

LFA-3 expression is elevated in lesions present in the buccal mucosa of patients having oral lichen planus (OLP) and it thus implicated in the pathogenesis of OLP (Kirby et al., *Oral Dis.*, 1995, 1, 193). Accordingly, treatment of individuals with the antisense compounds of the invention is expected to limit the growth and spread of OLP.

D. Combination Therapies and Compositions

1. Combinations of Antisense Compounds

Two or more antisense compounds can be administered simultaneously as described above. Combination treatments can also be carried out by first (1) administering a first composition comprising one or more antisense compounds targeted to one or more CAMs (or a combination thereof with one or more anti-inflammatory/immunosuppressive or chemotherapeutic agents) for a first period of time and then (2) "switching" to administration of a second composition comprising one or more antisense compounds targeted to one or more CAMs (or a combination thereof with one or more anti-inflammatory or chemotherapeutic agents) for a second period of Lime. Whether administered simultaneously or sequentially, preferred pairings of antisense compounds include those targeted to molecules that mediate cellular adhesion, such as: (1) LFA-3 and ICAM-1; (2) LFA-3 and VCAM-1; (3) LFA-3 and ELAM-1; and (4) LFA 3 and a B7 protein, such as B7-1 or B7-2. Because B7-1 and LFA-3 act in a co-stimulatory manner to activate T cells (Parra et al., *J. Immunol.*, 1997, 158, 637; Parra et al., *Mol. Cell. Biol.*, 17, 1314), combination (4) is particularly preferred for modulating T cell activation. Antisense compounds targeted to ICAM-1, VCAM-1, ELAM-1 and B7 proteins are described in U.S. Pat. Nos. 5,514,788 and 5,591,623, and copending U.S. patent application Ser. No. 08/777,266, filed Dec. 31, 1996, all to Bennett et al.

If desired, the therapeutic antisense modulation of the expression of LFA-3 (or another CAM) can be combined with additional therapies in order to achieve a requisite level of interference with, or prevention of, undesirable disorders or diseases. Such combinations can be carried out, for example, by simultaneously administering (a) two or more antisense compounds targeted to two or more CAMs, (b) two or more antisense compounds, one targeted to a CAM and one another genetic target or (c), when treating an animal having inflammation, an antisense compound targeted to a CAM in combination with a non-antisense-based anti-inflammatory or immunosuppressive agent. If an animal having a hyperproliferative disease or disorder is to be treated, the antisense compound targeted to a CAM may be combined with a non-antisense-based chemotherapeutic agent. When used with the antisense compounds of the invention, such non-antisense-based agents (NABAs) may be used in simple combination (e.g., administration of a NABA and an antisense compound), sequentially (e.g., administration of a first NABA and an antisense compound for a period of time followed by administration of a second NABA and an antisense compound), or in combination with one or more other such non-antisense-based agents or physical treatments (e.g., administration of a NABA and an antisense compound, or, in the treatment of hyperproliferative disorders for example, administration of one or more NABAs and antisense compounds in combination with radiotherapy). When two (or more) antisense compounds, or a combination of one or more antisense compounds and one or more NABAs, are to be administered simultaneously in a treatment regime, one preferred composition is one comprising a lipid vesicle, particularly a sterically stabilized lipid vesicle, comprising both (or all) of the compounds. In the context of the invention, the term "treatment regimen" is meant to encompass therapeutic, palliative and prophylactic modalities.

For antiviral uses, the antisense compounds of the invention may be combined with antisense compounds directed against a specific virus of interest. For example, for in vivo or ex vivo treatment of CMV infected cells, the antisense compounds may be combined with one or more antisense compounds targeted to CMV. Particularly preferred antisense compounds targeted to CMV, and therapeutic methods of use thereof, are described in U.S. Pat. Nos. 5,442,049 and 5,595,978, hereby incorporated by reference. Particularly preferred antisense compounds to HIV are described in U.S. Pat. Nos. 5,166,195 and 5,591,623, also hereby incorporated by reference. One or more non-antisense based antiviral agents, such as ganciclovir and foscarnet, may also be combined with one or more of the antisense compounds of the invention. Other non-antisense based antiviral agents preferably combined with the antisense compounds of the invention include those described in U.S. Pat. No. 5,523,389 and 5,627,185, hereby incorporated by reference, and published PCT application WO 96/40164.

2. Combinations with Chemotherapeutic Agents

For the purpose of treating hyperproliferative disorders, the antisense compounds of the invention can additionally or alternatively be used in combination with non-antisense-based chemotherapeutic agents. Examples of such agents that can be used in combination with the antisense compounds of the invention include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, nitrogen mustards, methylcyclohexylnitrosurea, melphalan, cyclophosphamide, 6-mercaptopurine, 6-thioguanine, cytarabine (CA), 5-azacytidine, hydroxyurea, deoxycoformycin, 5-fluorouracil (5-FU), 4-hydroxyperoxycyclophosphoramide, 5-fluorodeoxyuridine (5-FUdR), methotrexate (MTX), colchicine, vincristine, vinblastine, etoposide, trimetrexate, teniposide, cisplatin and diethylstilbestrol (DES). (See, generally, *The Merck Manual of Diagnosis and Therapy*, 15th Ed., pp. 1206–1228, Berkow et al., eds., Rahay, N.J., 1987).

3. Combinations with Anti-Inflammatory/Immunosuppressive Agents

Examples of non-antisense-based anti-inflammatory or immunosuppressive agents that can be used in combination with the antisense compounds of the invention include but are not limited to salicylates; nonsteroidal anti-inflammatory drugs (NSAIDs), including indomethacin, ibuprofen, fenopofen, ketoprofen, naproxen, piroxicam, phenylbutazone, oxyphenbutazone, sulindac and meclofenamate; gold compounds, such as auranofin; D-penicillamine; cyclophosphamide; methotrexate; azathioprine; colchicine; hydroxychloroquine; corticotropin; steroids and corticosteroids such as, for example, hydrocortisone, deoxyhydrocortisone, fludrocortisone, prednisolone, methylprednisolone, prednisone, triamcinolone, dexamethasone, betamethasone and paramethasone. See, generally, *The Merck Manual of Diagnosis and Therapy*, 15th Ed., pp. 1239–1267 and 2497–2506, Berkow et al., eds., Rahay, N.J., 1987).

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
        (A) LENGTH: 1040 base pairs
        (B) TYPE: Nucleic Acid
        (C) STRANDEDNESS: Single
        (D) TOPOLOGY: Unknown (iv) ANTI-SENSE: No (x) PUBLICATION INFORMATION:
        (A) AUTHORS: Wallner, B.P.
             Frey, A.Z.
             Tizard, R.
             Mattaliano, R.J.
             Hession, C.
             Sanders, M.E.,
             Dustin, M.L.
             Springer, T.A.
        (B) TITLE: Primary structure of lymphocyte
             function-associated antigen 3 (LFA-3). The ligand
             of the T lymphocyte CD2 glycoprotein.
        (C) JOURNAL: J. Exp. Med.
        (D) VOLUME: 166
        (E) ISSUE: 4
        (F) PAGES: 923-932
        (G) DATE: 01-OCT-1987

(xi) SEQUENCE DESCRIPTION: SEQ ID NO: 1:

| | |
|---|---:|
| CGACGAGCCA TGGTTGCTGG GAGCGACGCG GGGCGGGCCC TGGGGGTCCT | 50 |
| CAGCGTGGTC TGCCTGCTGC ACTGCTTTGG TTTCATCAGC TGTTTTTCCC | 100 |
| AACAAATATA TGGTGTTGTG TATGGGAATG TAACTTTCCA TGTACCAAGC | 150 |
| AATGTGCCTT TAAAAGAGGT CCTATGGAAA AAACAAAAGG ATAAAGTTGC | 200 |
| AGAACTGGAA AATTCTGAAT TCAGAGCTTT CTCATCTTTT AAAAATAGGG | 250 |
| TTTATTTAGA CACTGTGTCA GGTAGCCTCA CTATCTACAA CTTAACATCA | 300 |
| TCAGATGAAG ATGAGTATGA AATGGAATCG CCAAATATTA CTGATACCAT | 350 |
| GAAGTTCTTT CTTTATGTGC TTGAGTCTCT TCCATCTCCC ACACTAACTT | 400 |
| GTGCATTGAC TAATGGAAGC ATTGAAGTCC AATGCATGAT ACCAGAGCAT | 450 |
| TACAACAGCC ATCGAGGACT TATAATGTAC TCATGGGATT GTCCTATGGA | 500 |
| GCAATGTAAA CGTAACTCAA CCAGTATATA TTTTAAGATG GAAAATGATC | 550 |
| TTCCACAAAA AATACAGTGT ACTCTTAGCA ATCCATTATT TAATACAACA | 600 |
| TCATCAATCA TTTTGACAAC CTGTATCCCA AGCAGCGGTC ATTCAAGACA | 650 |
| CAGATATGCA CTTATACCCA TACCATTAGC AGTAATTACA ACATGTATTG | 700 |
| TGCTGTATAT GAATGGTATT CTGAAATGTG ACAGAAAACC AGACAGAACC | 750 |
| AACTCCAATT GATTGGTAAC AGAAGATGAA GACAACAGCA TAACTAAATT | 800 |
| ATTTTAAAAA CTAAAAAGCC ATCTGATTTC TCATTTGAGT ATTACAATTT | 850 |
| TTGAACAACT GTTGGAAATG TAACTTGAAG CAGCTGCTTT AAGAAGAAAT | 900 |
| ACCCACTAAC AAAGAACAAG CATTAGTTTT GGCTGTCATC AACTTATTAT | 950 |
| ATGACTAGGT GCTTGCTTTT TTTGTCAGTA AATTGTTTTT ACTGATGATG | 1000 |
| TAGATACTTT TGTAAATAAA TGTAAATATG TACACAAGTG | 1040 |

(2) INFORMATION FOR SEQ ID NO: 2:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 2:

CCGCGTCGCT CCCAGCAACC                                    20

(2) INFORMATION FOR SEQ ID NO: 3:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 3:

GGCAGACCAC GCTGAGGACC                                    20

(2) INFORMATION FOR SEQ ID NO: 4:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 4:

AAGGCACATT GCTTGGTACA                                    20

(2) INFORMATION FOR SEQ ID NO: 5:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 5:

TGAGGCTACC TGACACAGTG                                    20

(2) INFORMATION FOR SEQ ID NO: 6:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 6:

ATTGGAGTTG GTTCTGTCTG                                    20

(2) INFORMATION FOR SEQ ID NO: 7:

(i) SEQUENCE CHARACTERISTICS:
        (A) LENGTH: 20 base pairs (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 7:

TCATCTTCTG TTACCAATCA                                            20

(2) INFORMATION FOR SEQ ID NO: 8:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 8:

AATTTAGTTA TGCTGTTGTC                                            20

(2) INFORMATION FOR SEQ ID NO: 9:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 9:

TACATTTCCA ACAGTTGTTC                                            20

(2) INFORMATION FOR SEQ ID NO: 10:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 10:

TGCTTGTTCT TTGTTAGTGG                                            20

(2) INFORMATION FOR SEQ ID NO: 11:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 11:

ATAATAAGTT GATGACAGCC                                            20

(2) INFORMATION FOR SEQ ID NO: 12:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes

```
        (xi) SEQUENCE DESCRIPTION: SEQ ID NO: 12:

AAGCAAGCACC TAGTCATAT                                              20

(2) INFORMATION FOR SEQ ID NO: 13:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: No (xi) SEQUENCE DESCRIPTION: SEQ ID NO: 13:

GCTGAGCCTTA GCAAGCAGT                                              20

(2) INFORMATION FOR SEQ ID NO: 14:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: No (xi) SEQUENCE DESCRIPTION: SEQ ID NO: 14:

GTGCCCTGCC CACCGACCAC                                              20

(2) INFORMATION FOR SEQ ID NO: 15:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: No (xi) SEQUENCE DESCRIPTION: SEQ ID NO: 15:

AGTGCGCATG TCAACGACGT                                              20

(2) INFORMATION FOR SEQ ID NO: 16:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (xi) SEQUENCE DESCRIPTION: SEQ ID NO: 16:

TGCATCCCCC AGGCCACCAT                                              20

(2) INFORMATION FOR SEQ ID NO: 17:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: No (xi) SEQUENCE DESCRIPTION: SEQ ID NO: 17:

CAGCGTGGTC TGCCTGCTGC                                              20
```

(2) INFORMATION FOR SEQ ID NO: 18:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 18:

```
GTTATGCTGT TGTCTTCATC                                             20
```

(2) INFORMATION FOR SEQ ID NO: 19:

(i) SEQUENCE CHARACTERISTICS:
        (A) LENGTH: 41 base pairs
        (B) TYPE: Nucleic Acid
        (C) STRANDEDNESS: Single
        (D) TOPOLOGY: Linear (iv) ANTI-SENSE: No (xi) SEQUENCE DESCRIPTION: SEQ ID NO: 19:

```
TGATTGGTAA CAGAAGATGA AGACAACAGC ATAACTAAAT T                     41
```

What is claimed is:

1. An antisense compound comprising from about 20 nucleotides connected by covalent linkages, wherein said antisense compound comprises a nucleobase sequence selected from the group consisting of SEQ ID NO: 4, 5, 7, 8 or 9, wherein said antisense compound inhibits the expression of human lymphocyte function-associated antigen 3.

2. The antisense compound of claim 1 wherein said antisense compound specifically binds to a sequence contained within SEQ ID NO: 19.

3. The antisense compound of claim 1 wherein said antisense compound comprises one or more chemical modifications selected from the group consisting of one or more modified linkages, one or more modified nucleobases and one or more sugar modifications.

4. An in vitro method of blocking or limiting the interaction of lymphocyte function-associated antigen 3 and CD2 comprising contacting cells expressing lymphocyte function associated antigen 3 in vitro with one or more antisense compounds of claim 1.

5. An in vitro method of limiting, blocking or preventing T cell stimulation or activation by cells expressing LFA-3 comprising contacting cells expression LFA-3 in vitro with an effective amount of one or more of the antisense compounds of claim 1.

\* \* \* \* \*

UNITED STATES PATENT AND TRADEMARK OFFICE
CERTIFICATE OF CORRECTION

PATENT NO. : 6,001,651
DATED : December 14, 1999
INVENTOR(S) : Bennett et al.

It is certified that error appears in the above-identified patent and that said Letters Patent is hereby corrected as shown below:

Column 1,
Line 37, please delete "FASEE" and insert -- FASEB --.

Column 13,
Line 23, please delete "Lherefore" and insert -- therefore --.

Column 17,
Line 38, please delete "C-a" and insert -- C-α --.

Column 34,
Line 30, please delete "CHCl" and insert -- $CHCl_3$ --.

Column 38,
Line 36, please delete "LPA-3" and insert -- LFA-3 --.

Column 40,
Line 45, please delete "<" and insert -- $\leq$ --.

Column 41,
Line 26, please delete "radiolablled" and insert -- radiolabelled --.

Column 42,
Line 67, please delete "TSIS" and insert -- ISIS --.

Column 43,
Line 33, following "20-25", please insert -- % --.
Line 49, please delete "IF6" and insert -- IE6 --.
Line 53, please delete "TgC1" and insert -- IgG1 --.

Column 44,
Line 34, please delete "EC&C" and insert -- EC&G --.

Column 48,
Line 24, please delete "Tnt." and insert -- Int. --.

UNITED STATES PATENT AND TRADEMARK OFFICE
CERTIFICATE OF CORRECTION

PATENT NO. : 6,001,651
DATED : December 14, 1999
INVENTOR(S) : Bennett et al.

It is certified that error appears in the above-identified patent and that said Letters Patent is hereby corrected as shown below:

Column 60,
Line 37, please delete "expression" and insert -- expressing --.

Signed and Sealed this

Twenty-fifth Day of December, 2001

Attest:

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,001,651
DATED : December 14, 1999
INVENTOR(S) : Bennett et al.

Page 1 of 1

It is certified that error appears in the above-identified patent and that said Letters Patent is hereby corrected as shown below:

<u>Title page,</u>
Item [73], add -- Yale University, New Haven, Conn. --

Signed and Sealed this

Twenty-first Day of May, 2002

Attest:

Attesting Officer

JAMES E. ROGAN
*Director of the United States Patent and Trademark Office*